US006472148B1

(12) United States Patent
Bamdad et al.

(10) Patent No.: US 6,472,148 B1
(45) Date of Patent: *Oct. 29, 2002

(54) MOLECULAR RECOGNITION AT SURFACES DERIVATIZED WITH SELF-ASSEMBLED MONOLAYERS

(75) Inventors: Cynthia C. Bamdad, San Marino, CA (US); George B. Sigal, Rockville, MD (US); Jack L. Strominger, Lexington, MA (US); George M. Whitesides, Newton, MA (US)

(73) Assignee: President and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/786,187

(22) Filed: Jan. 21, 1997

Related U.S. Application Data

(63) Continuation-in-part of application No. 08/312,388, filed on Sep. 26, 1994, now Pat. No. 5,620,850.

(51) Int. Cl.$^7$ ................................................ C12Q 1/68
(52) U.S. Cl. .......................................... 435/6; 536/243
(58) Field of Search ............................... 435/6; 536/24.3

(56) References Cited

U.S. PATENT DOCUMENTS

| | | | |
|---|---|---|---|
| 2,905,539 A | 9/1959 | Bowerman | 174/250 |
| 4,877,830 A | 10/1989 | Döbeli et al. | 525/54.3 |
| 4,964,972 A | 10/1990 | Sagiv et al. | 204/418 |
| 5,032,216 A | 7/1991 | Felten | 156/628 |
| 5,047,513 A | 9/1991 | Döbeli et al. | 530/412 |
| 5,200,471 A | 4/1993 | Coleman et al. | 525/326.9 |
| 5,238,808 A | 8/1993 | Bard et al. | 435/4 |
| 5,242,828 A | 9/1993 | Bergström et al. | 435/291 |
| 5,250,188 A | 10/1993 | Bruening et al. | 210/672 |
| 5,259,926 A | 11/1993 | Kuwabara et al. | 156/659.1 |
| 5,284,933 A | 2/1994 | Döbeli et al. | 530/350 |
| 5,294,369 A | 3/1994 | Shigekawa et al. | 252/313.1 |
| 5,324,457 A | 6/1994 | Zhang et al. | 252/700 |
| 5,436,161 A | 7/1995 | Bergström et al. | 435/291 |
| 5,472,881 A | * 12/1995 | Beebe et al. | 436/94 |
| 5,512,131 A | 4/1996 | Kumar et al. | 156/655.1 |
| 5,591,578 A | 1/1997 | Meade et al. | 435/6 |
| 5,795,714 A | * 8/1998 | Cantor et al. | 435/6 |

FOREIGN PATENT DOCUMENTS

| | | |
|---|---|---|
| DE | 42 19 159 | 12/1993 |
| DE | 0515615 | 9/1996 |
| EP | 0 589 867 | 5/1990 |
| EP | 0 664 452 | 7/1995 |
| EP | 0 698 787 | 2/1996 |
| EP | 0 515 615 | 9/1996 |
| JP | 6-41183 | 3/1994 |
| WO | 90/05303 | 5/1990 |
| WO | 92/10757 | 6/1992 |
| WO | 95/15971 | 6/1995 |
| WO | 96/40712 | 12/1996 |

OTHER PUBLICATIONS

Sigal et al., "A Self–Assembled Monolayer for the Binding and Study of histidine–Tagged Proteins by Surface Plasmon Resonance," *Analytical Chemistry*, 68(3):490–497 (1996).

Hsung et al., "Synthesis and Characterization of Unsymmetric Ferrocene–Terminated Phenylethynyl Oligomers $Cp_2Fe$–$[C\equiv C$–$C_6H_4]_n$–X (X –SH, sMe, SOMe, and $SO_2ME$)" *Organometallics*, 14:4808–4815 (1995).

Hegner et al., "Immobilizing DNA on Fold via Thiol Modification for Atomic Force Microscopy Imaging in Buffer Solutions," *FEBS*, 336(3):452–456 (1993).

Chrisey et al., "Covalent Attachment of Synthetic DNA to Self–Assembled Monolayer Films," *Nucleic Acids Research*, 24(15):3031–3035 (1996).

Kumar et al., "Patterning Self–Assembled Monolayers: Applications in Materials Science," *Langmuir* 10:1498–1511 (1994).

Spinke et al., "Molecular Recognition at Self–Assembled monlayers: Optimization of Surface Functionalization," *J. Chem. Phys.* 99(9):7012–7019 (1993).

Schierbaum et al., "Molecular Recognition by Self–Assembled Monolayers of Cavitand Receptors," *Science*, 265: 1413–1415 (Sep. 2, 1994).

Spinke et al., "Molecular Recognition at Self–Assembled Monolayers: The Construction of Multicomponent Multilayers," *Langmuir* 9:1821–1825 (1993).

Prime et al., "Adsorption of Proteins onto Surfaces Containing End–Attached Oligo(ethylene oxide): A Model System Using Self–Assembled Monolayers," *J. Am. Chem. Soc.*, 115:10714–10721 (1993).

Chaiken et al., "Analysis of Macromolecular Interactions Using Immobilized Ligands," *Analytical Biochemistry* 201:197–210 (1992).

Gentz et al., "Bioassay for Trans–Activation using Purified Human Immunodeficiency Virus tat–encoded Protein: Trans–Activation Requires mRNA Synthesis," *Proc. Natl. Acad. Sci. USA*, 86:821–824 (1989).

(List continued on next page.)

*Primary Examiner*—Kenneth R. Horlick
(74) *Attorney, Agent, or Firm*—Robin M. Silva; Renee M. Kosslak; Altritton & Herbert LLP

(57) ABSTRACT

An article suitable for use as a biosensor includes a molecule of a formula X—R—Ch adhered to a surface of the article as part of a self-assembled monolayer. X is a functionality that adheres to the surface, R is a spacer moiety, and Ch is a chelating agent. A metal ion can be coordinated by the chelating agent, and a polyamino acid-tagged biological binding partner of a target biological molecule coordinated to the metal ion. A method of the invention involves bringing the article into contact with a medium containing or suspected of containing the target biological molecule and allowing the biological molecule to biologically bind to the binding partner. The article is useful particularly as a surface plasmon resonance chip.

14 Claims, 9 Drawing Sheets

OTHER PUBLICATIONS

Jönsson et al., "Biosensors Based on Surface Concentration Measuring Devices—The Concept of Surface Concentration," *Progr. Colloid & Polymer Sci.* 70:96–100 (1985).

Davis et al., "Continuous Liquid–Phase Piezeolectric Biosensor for Kinetic Immunoassays," *Anal. Chem.* 61:1227–1230 (1989).

Yaw et al., "Electrogenerated Chemiluminescence. 53. Electrochemistry and Emission from Adsorbed Monolayers of a Tris(bipyridyl)ruthenium(II)–Based Surfactant on Gold and Tin Oside Electrodes," *Langmuir* 7(1):195–201 (1991).

Milan et al., "Enhanced Sequence Specific Recognition in the Minor Grooove of DNA by Covalent Peptide Dimers: Bis(pyridine–2–carboxamidonetropsin)($CH_2$)$_{3-6}$," *J. Am. Chem. Soc.* 115:9892–9899 (1993).

Parikh et al., "An Intrinsic Relationship Between Molecular Structure in Self–Assembled n–Alkysiloxane Monolayers and Deposition Temperature," *J. Phys. Chem.* 98:7577–7590 (1994).

Smith et al., "Kinetically Inert Co(III) Linkage through an Engineered Metal Binding Site: Specific Orientation of Tecombinant human Papillomavirus Type 16 E7 Protein on a Solid Support," *Methods: A Companion to Methods in Enzymology*, 4:73–78 (1992).

Hochuli et al., "New Metal Chelate Adsorbent Selective for Proteins and peptides Containing Neighbouring Histidine Residues," *Journal of Chromatography*, 411:177–184 (1987).

Löfås et al., "A Novel Hydrogel matrix on Gold Surfaces in Surface Plasmon Resonance Sensors for Fast and Efficient Covalent Immobilization of Ligands," *J. Chem., Soc. Chem. Commun.*, 1526–1528 (1990).

Kasher et al., "One–Step Purification of Recombinant Human Papillomavirus Type 16 E7 Oncoprotein and Its Binding to the Retinoblastoma Gene Product," *Bio Techniques* 14(4): 630–641 (1993).

Laibinis et al., "Orthogonal Self–Assembled Monolayers: Alkanethiols on Gold and Alkane Carboxylic Acids on Alumina," *Reports*, 845–847 (Aug. 25, 1989).

Bain et al., "Formation of Monolayers by the Coadsorption of Thiols on Gold: Variation in the Length of the Alkyl Chain," *J. Am. Chem. Soc.*, 111:7164–7175 (1989).

Kumar et al., "Patterning Self–Assembled Monolayers: Applications in Materials Science," *Langmuir*, 10:1498–1511 (1994).

Muramatsu et al., "Piezoelectric Immuno Sensor for the Detection of *Candida albicans* Microbes," *Analytica Chimica Acta*, 188:257–261 (1986).

Stenberg et al., "Quantitative Determination of Surface Concentration of Protein with Surface Plasmon Resonance Using Radiolabeled Proteins," *Journal of Colloid and Interface Science*, 143(2):513–526 (1991).

McGovern et al., "Role of Solvent on the Silanization of Glass with Octadecyltrichlorosilane," *Langmuir*, 10:3607–3614 (1994).

Kumar et al., "A Simple Method for Introducing –SH/COOH Group at 5'–CH end of Oligonucleotide," *Nucleosides & Nucleotides*, 11(5):999–1002 (1992).

Vigmond et al., "Site–Specific Immobilization of Molecularly Engineered Dihydrofolate Reductase to Gold Surfaces," *Langmuir*, 10:2860–2862 (1994).

Shnek et al., "Specific Protein Attachemtn to Artificial Membranes via Coordination to Lipik–Bound Copper (II)," *Langmuir*, 10:2382–2388 (1994).

Dwyer et al., "Structural Analysis of Covalent Peptide Dimers, Bis(pyridine–2–carboxamidonetropsin)($CH_2$)$_{3-6}$, in Complex with 5'–TGACT–3' Sites by Two Dimensional NMR," *J. Am. Chem. Soc.*, 115:9900–9906 (1993).

Kretschmann et al., "Radioactive Decay of Non Radiative Surface Plasmons Excited by Light," *Zeitschrift for Naturforschung*, 23A, 2135–2136 (1968).

Hoffman et al., "Purification of his–Tagged Proteins in Non–Denaturing Conditions Suggests a Convenient Method for Protein Interaction Studies," *Nuc. Acids Res.*, 19:6337–6338 (1991).

Van Ness et al., "A Versatile Solid Support System for Oligodeoxynucleotide Probe–Based Hybridization Assays," *Nucleic Acids Research*,19(2):3345–3350 (1991).

Xiao–Hong et al., "Immobilization of DNA on an Aluminum (III) Alkanebisphosphonate Thin Film with Electrogenerated Chemiluminescent Detection," *J. Am. Chem. Soc.*, 116:8386–8387 (1994).

* cited by examiner

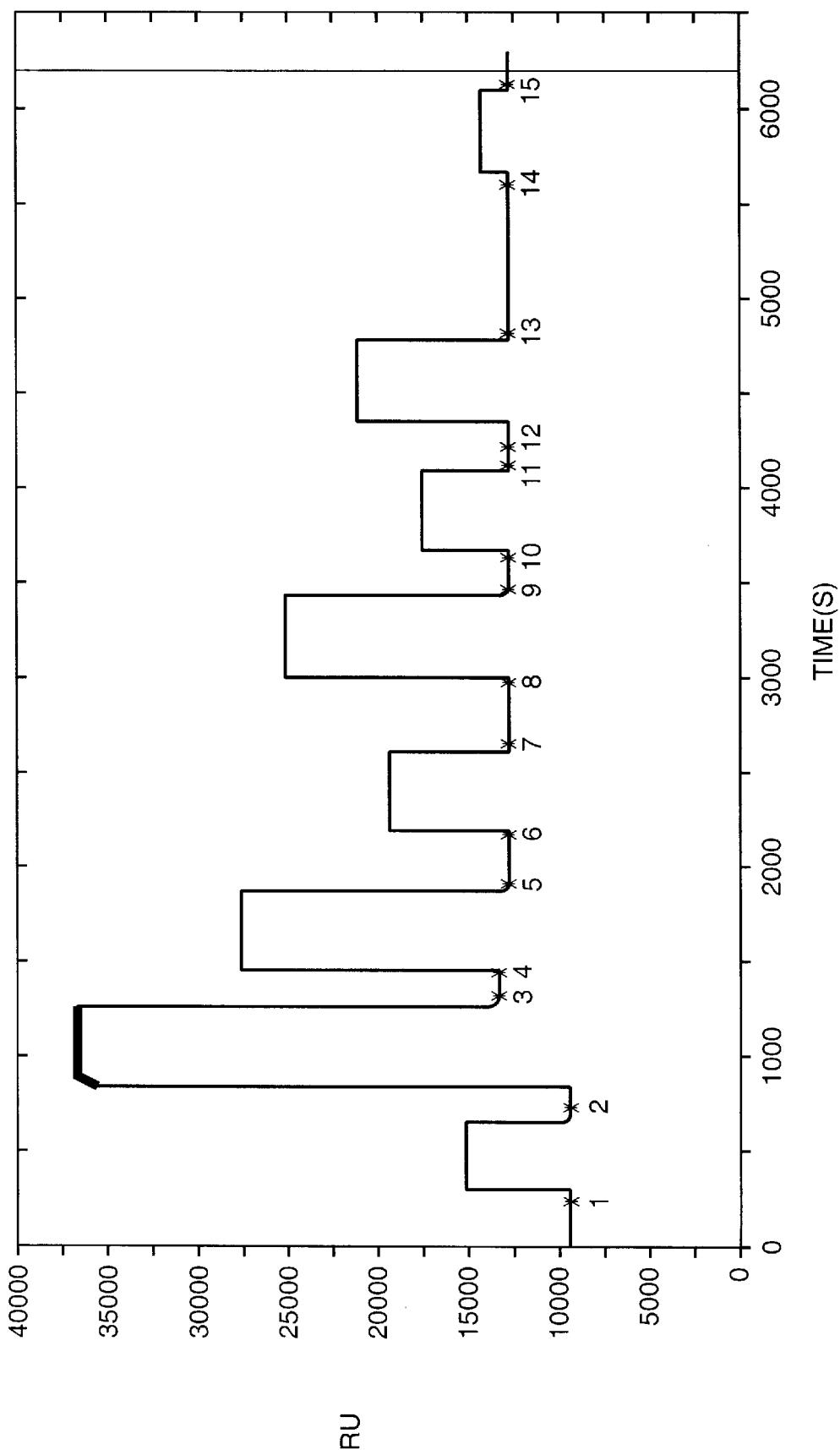
FIG._1

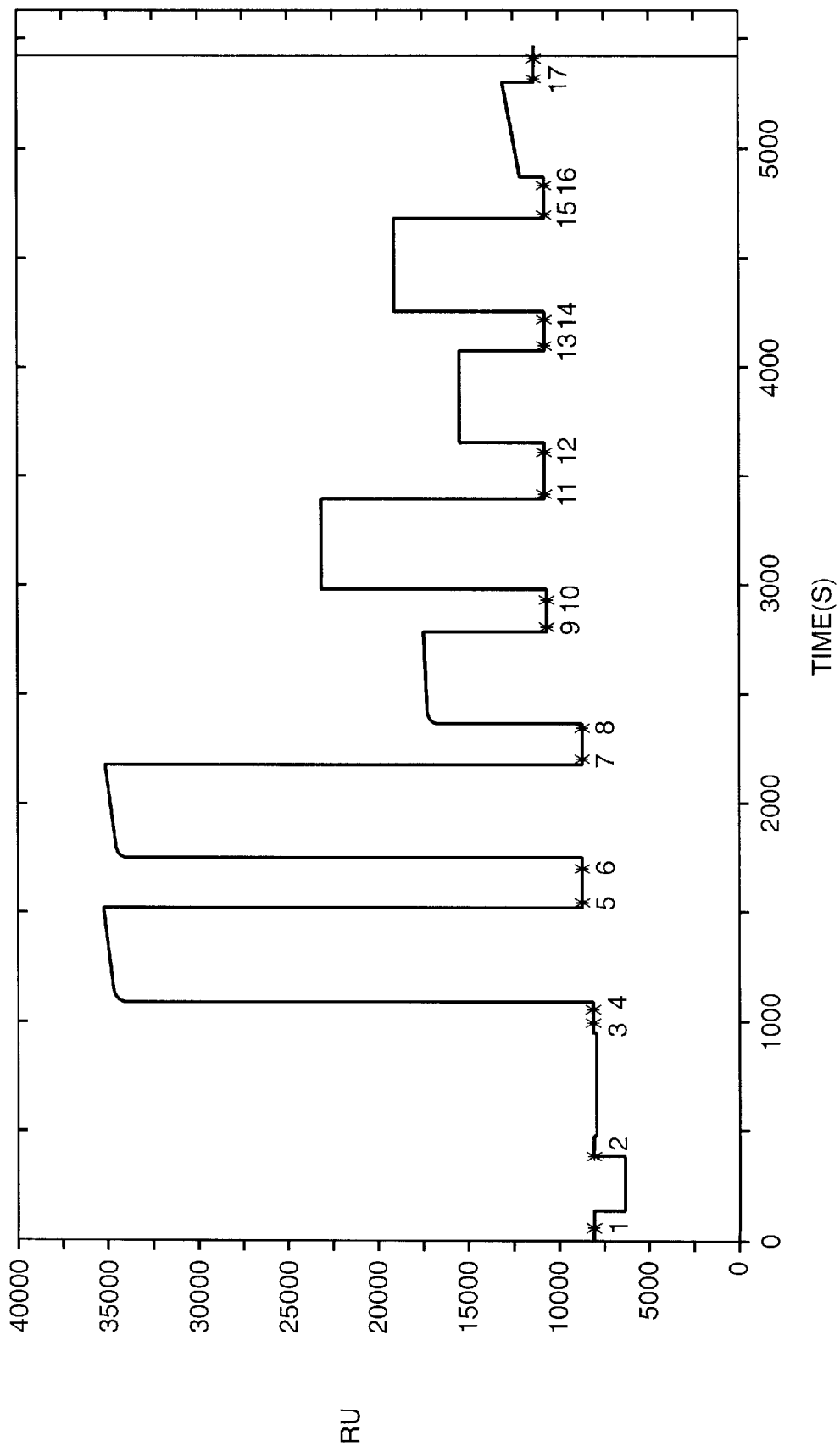
FIG._2

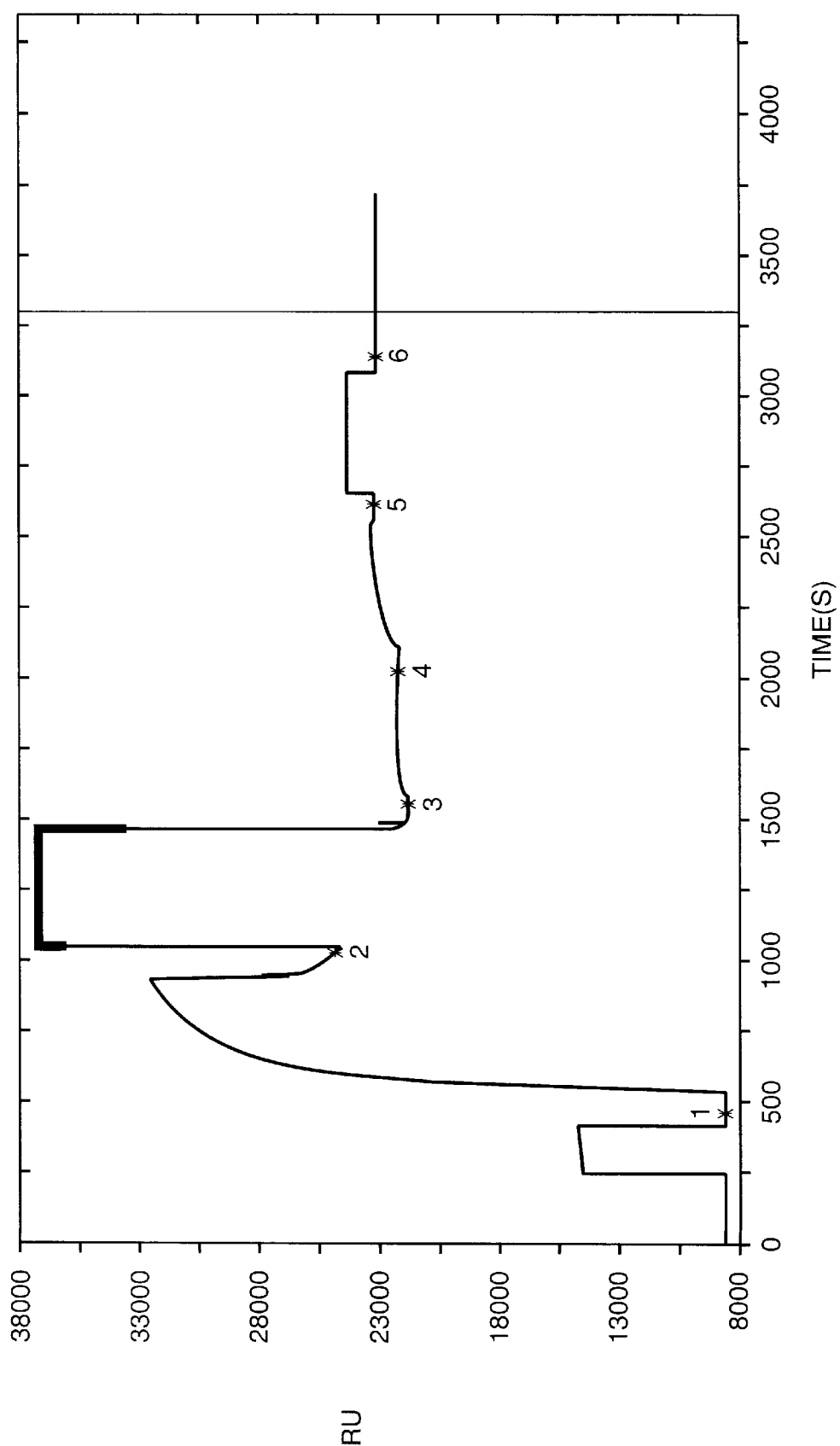
FIG._3

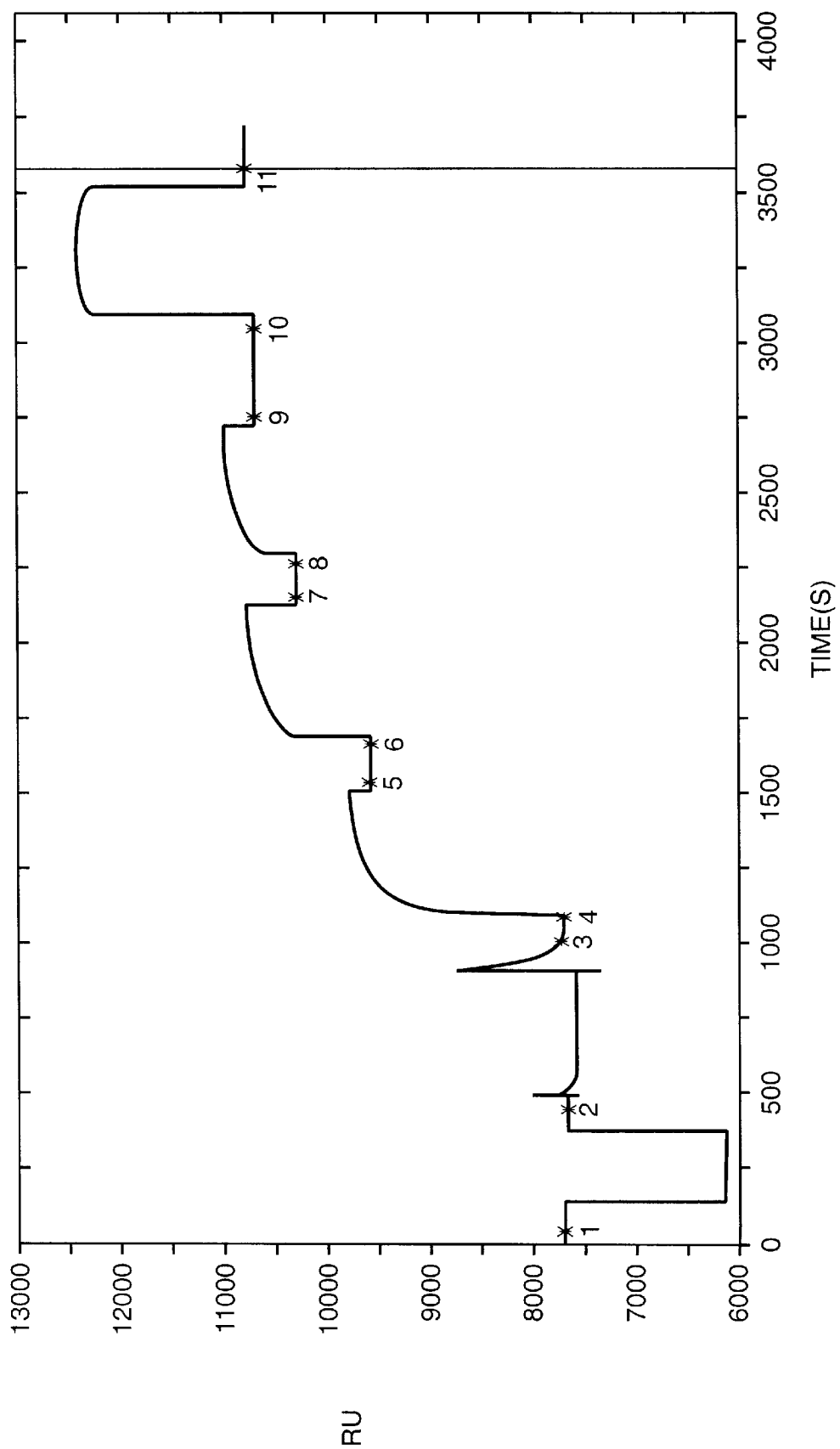
FIG._4

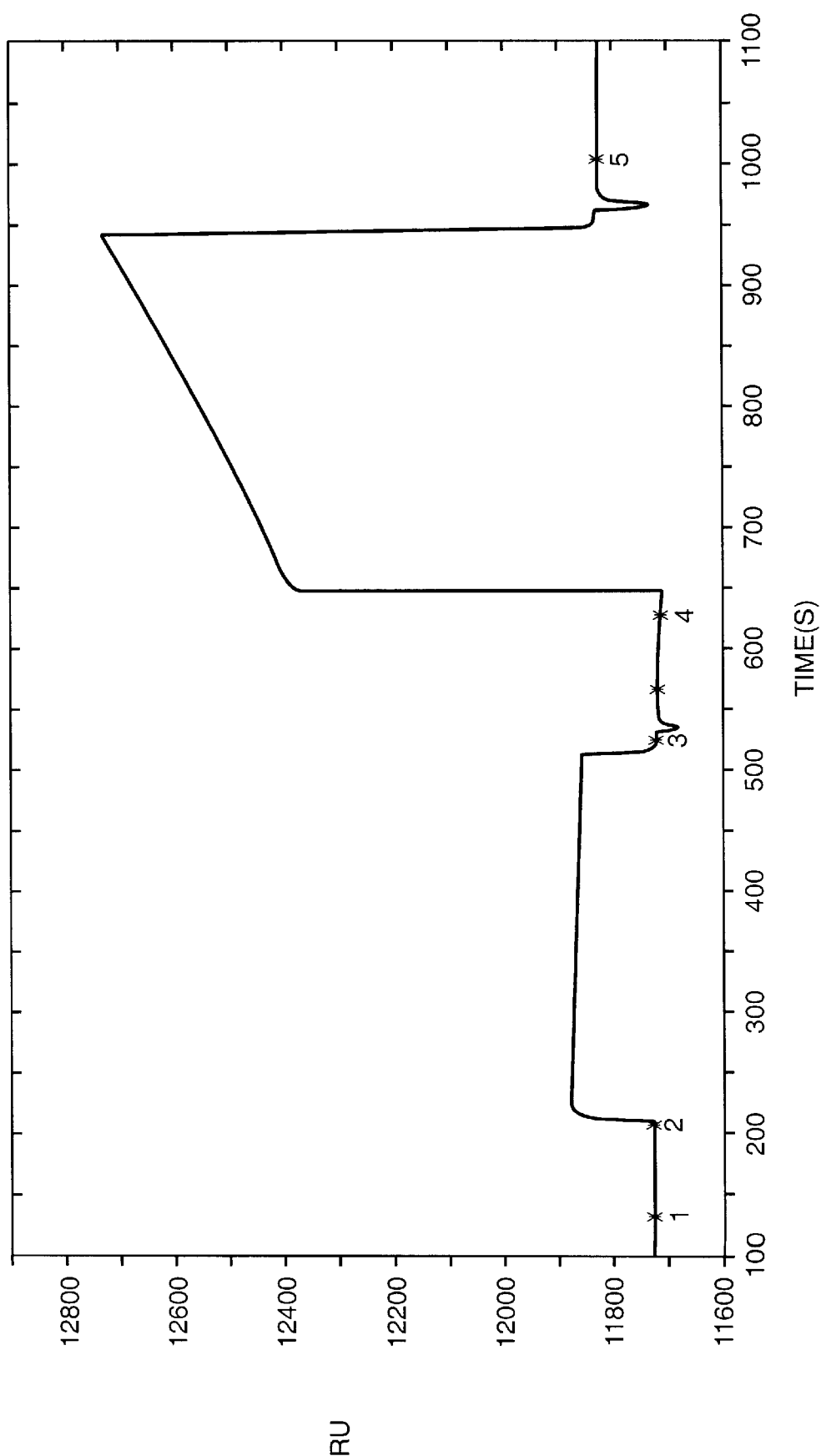
FIG._5

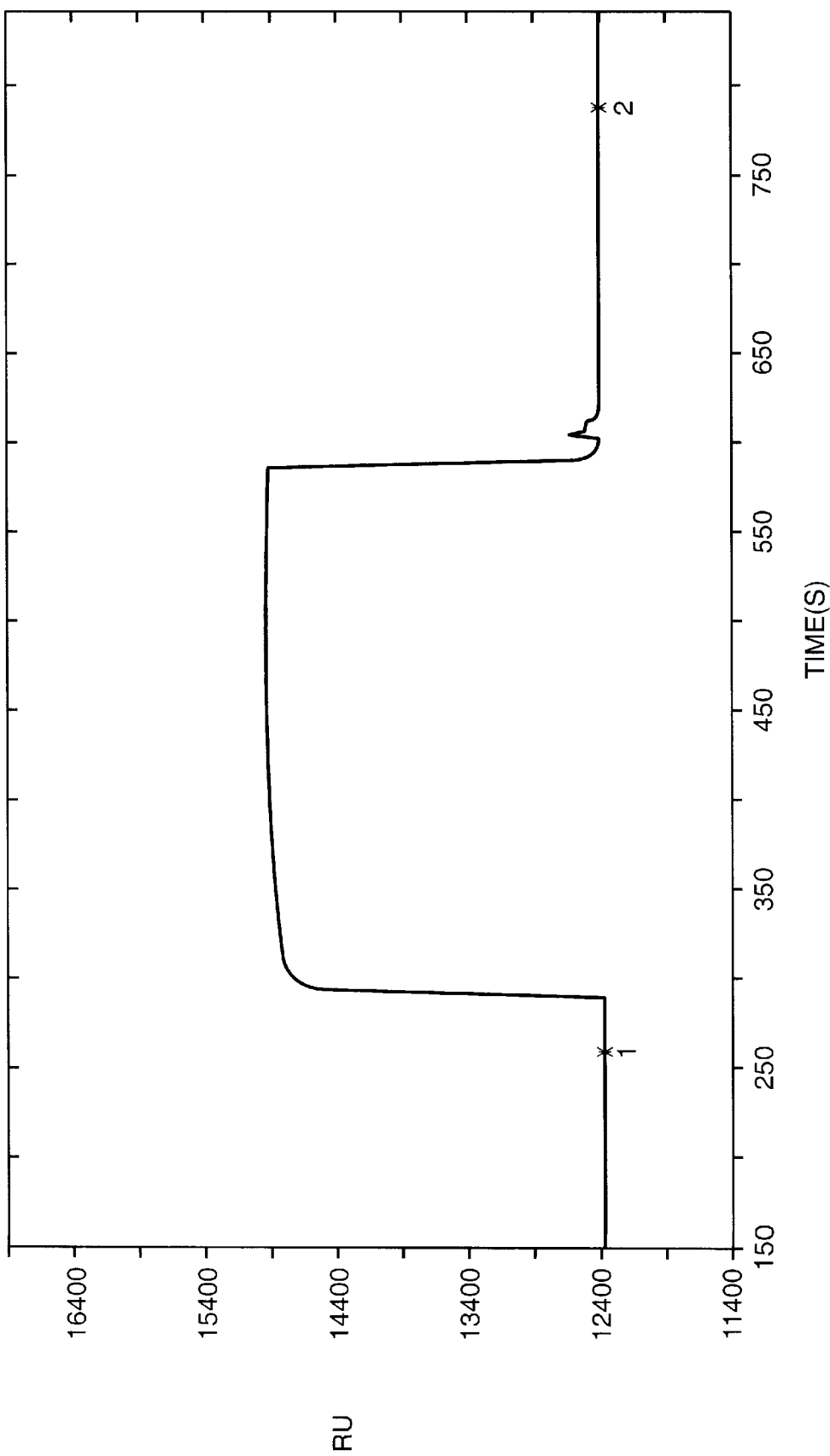
FIG._6

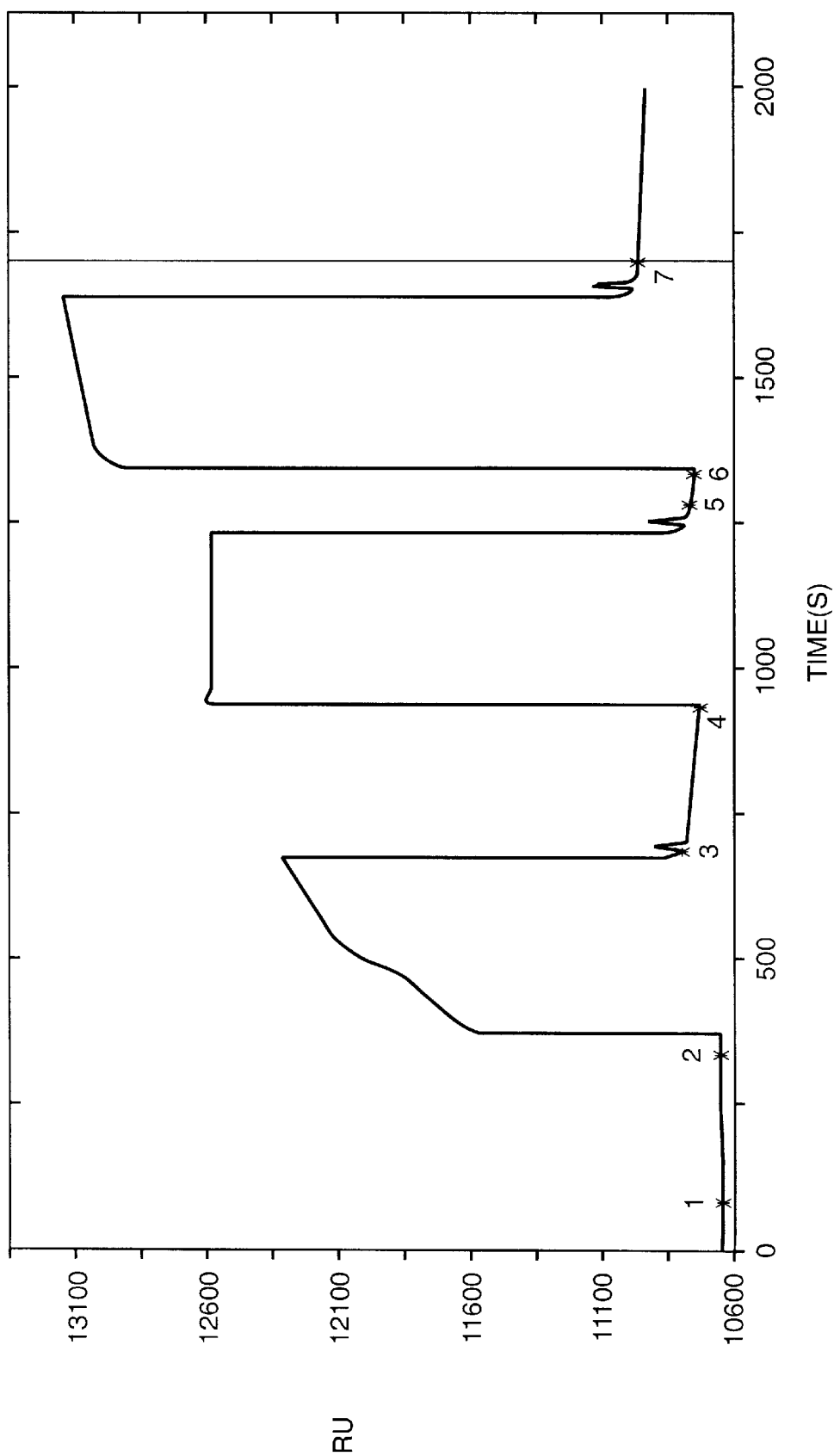
FIG._7

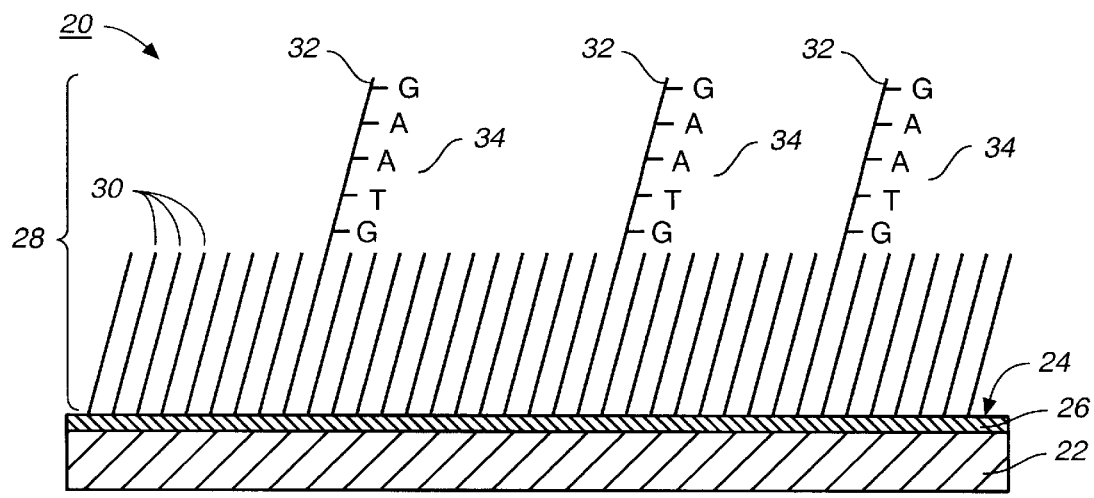
FIG._8
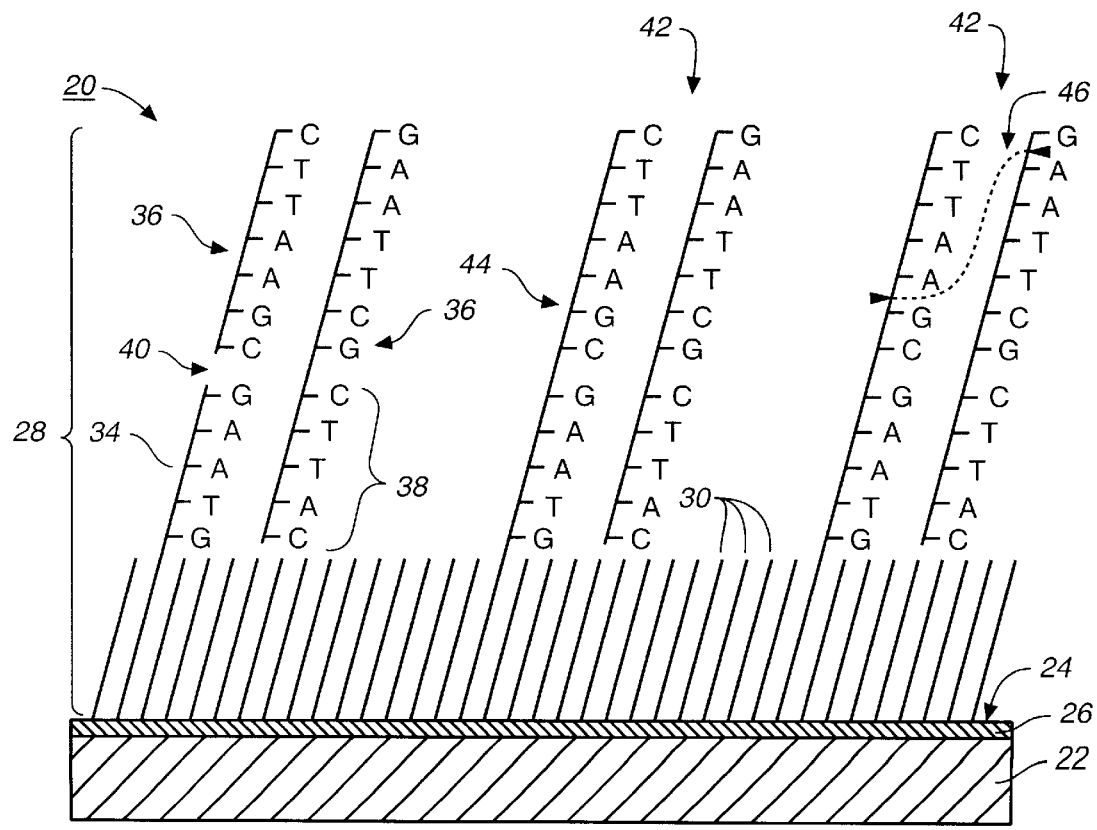
FIG._9

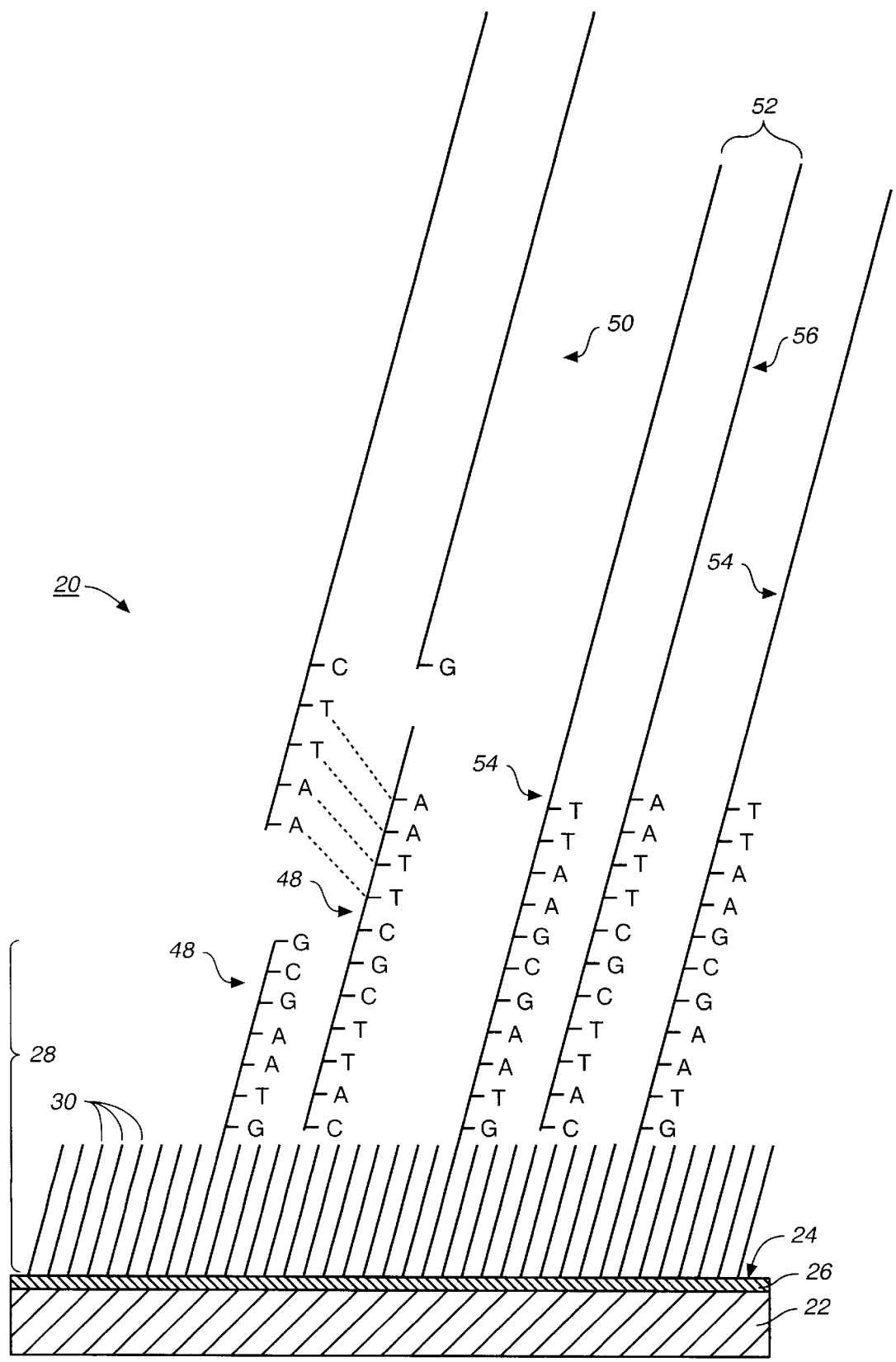
FIG._10

MOLECULAR RECOGNITION AT SURFACES DERIVATIZED WITH SELF-ASSEMBLED MONOLAYERS

RELATED APPLICATIONS

This application is a continuation-in-part of U.S. patent application Ser. No. 08/312,388, filed Sep. 26, 1994 by Bamdad, et al., now U.S. Pat. No. 5,620,850.

The United States Government has certain rights in this invention pursuant to grant numbers GM30367 and CA47554 from the National Institutes of Health.

FIELD OF THE INVENTION

The present invention relates generally to the derivatization of surfaces for determination of analytes, for example from a fluid medium using a biological binding partner of the analyte. More particularly, the invention relates to the formation on a metal surface of a self-assembled molecular monolayer that exposes a binding partner to an analyte medium in a manner such that analysis of high sensitivity obtains.

BACKGROUND OF THE INVENTION

Biochemical analyses are invaluable, routine tools in health-related fields such as immunology, pharmacology, gene therapy, and the like. In order to successfully implement therapeutic control of biological processes, it is imperative that an understanding of biological binding between various species is gained. Indeed, an understanding of biological binding between various species is important for many varied fields of science.

Many biochemical analytical methods involve immobilization of a biological binding partner of a biological molecule on a surface, exposure of the surface to a medium suspected of containing the molecule, and determination of the existence or extent of molecule coupling to the surface-immobilized binding partner.

One such technique recently introduced is surface plasmon resonance. This technique utilizes a glass slide having a first side on which is a thin metal film and a second side opposite the first side (known in the art as a sensor chip), a prism, a source of monochromatic and polarized light, a photodetector array, and an analyte channel that directs a medium suspected of containing an analyte to the exposed surface of the metal film. A face of the prism is separated from the second side of the glass slide (the side opposite the metal film) by a thin film of refractive index matching fluid. Light from the light source is directed through the prism, the film of refractive index matching fluid, and the glass slide so as to strike the metal film at an angle at which total internal reflection of the light results, and an evanescent field is therefore caused to extend from the prism into the metal film. This evanescent field can couple to an electromagnetic surface wave (a surface plasmon) at the metal film, causing surface plasmon resonance.

Coupling is achieved at a specific angle of incidence of the light with respect to the metal film (the SPR angle), at which the reflected light intensity goes through a minimum due to the resonance. This angle is determined by a photodetector array as the angle of reflectance and is highly sensitive to changes in the refractive index of a thin layer adjacent to the metal surface. Thus it is highly sensitive to coupling of an analyte to the surface of the metal film. For example, when a protein layer is adsorbed onto the metal surface from an analyte-containing medium delivered to the surface by the analyte channel, the SPR angle shifts to larger values, and this shift is measured by the photodetector array. An article by Stenberg, Persson, Roos, and Urbaniczky, entitled "Quantitative Determination of Surface Concentration of Protein with Surface Plasmon Resonance Using Radiolabeled Proteins", *Journal of Colloid and Interface Science*, 43:2, 513–526 (1991), and references therein, describe the technique of surface plasmon resonance. Instrumentation for analysis via surface plasmon resonance is available from Pharmacia Biosensor, Piscataway, N.J., under the trademark BIAcore™.

Although the introduction of SPR represents an extremely valuable contribution to the scientific community, current state-of-the-art SPR instrumentation lacks the sensitivity needed to detect and analyze certain biological interactions that are at the forefront of scientific inquiry. Experimentation conducted in connection with the instant invention has led to identification of several complications associated with prior art sensor chips, which complications hinder the sensitivity of current SPR techniques. According to one technique for immobilization of a binding partner of an analyte on a surface plasmon resonance sensor chip, long-chain hydroxyalkyl thiols are adsorbed onto a gold surface as a monolayer, the monolayer's exposed hydroxy groups are activated with epichlorohydrin under basic conditions to form epoxides, a carboxylated dextran gel layer is covalently attached to the monolayer, and a proteinaceous binding partner of an analyte is first electrostatically adsorbed onto the dextran gel layer and then covalently attached thereto. This technique is described in an article by Lofas and Johnsson entitled, "A Novel Matrix on Gold Surfaces in Surface Plasmon Resonance Sensors for Fast and Efficient Covalent Immobilization of Ligands", *J. Chem. Soc., Chem Comm.* 1526–1528 (1990).

The effectiveness of this approach is hindered by several factors. First, covalent attachment of the proteinaceous binding partner to the gel can affect the binding partner's viability, or activity. Second, covalent attachment of the binding partner to the gel can not be effected with control over the orientation of the binding partner with respect to the surface of the chip (and, importantly, with respect to an analyte-containing medium). Third, non-specific interactions at the gel are promoted by the negative charge that it carries.

According to another technique, a mixed monolayer of hydroxyl and biotin-terminated alkane thiols is prepared on a gold surface, streptavidin is bound to the surface-bound biotin, and biotin-labeled proteins, that are binding partners of analytes, then are attached to empty sites on the streptavidin. However, because biotin must be covalently attached to the protein, this approach lacks control over orientation of the binding partner with respect to the analyte medium, and inactivation of the proteinaceous binding partner due to the formation of covalent linkage can occur. This technique is described in an article by Spinke, Liley, Guder, Angermaier, and Knoll entitled, "Molecular Recognition at Self-Assembled Monolayers: The Construction of Multicomponent Multilayers", *Langmuir*, 9, 1821–1825 (1993).

Accordingly, a general purpose of the present invention is to provide an easily-synthesized chemical species that readily adheres to a surface, and that facilitates surface immobilization of a binding partner of a molecule desirably captured at the surface with a high degree of sensitivity and minimal to zero non-specific binding. It is another purpose of the invention to provide an article with a surface having a high degree of sensitivity for a biological molecule. Another purpose of the invention is to provide a method of capturing a biological molecule, for example at a biosensor surface, by exploiting biological binding interactions that are extremely sensitive to molecular conformation and molecular orientation.

Nomenclature

The following definitions are provided to facilitate a clear understanding of the present invention.

The term, "chelating agent" refers to an organic molecule having unshared electron pairs available for donation to a metal ion. The metal ion is in this way coordinated by the chelating agent. Two or more neighboring amino acids can act as a chelating agent.

The terms, "bidentate chelating agent", "tridentate chelating agent", and "quadradentate chelating agent" refer to chelating agents having, respectively, two, three, and four electron pairs readily available for simultaneous donation to a metal ion coordinated by the chelating agent.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo biological binding with a particular biological molecule. For example, Protein A is a binding partner of the biological molecule IgG, and vice versa.

The term "biological molecule" refers to a molecule that car undergo biological binding with a particular biological binding partner.

The term "recognition region" refers to an area of a binding partner that recognizes a corresponding biological molecule and that facilitates biological binding with the molecule, and also refers to the corresponding region on the biological molecule. Recognition regions are typified by sequences of amino acids, molecular domains that promote van der Waals interactions, areas of corresponding molecules that interact physically as a molecular "lock and key", and the like.

The term "coordination site" refers to a point on a metal ion that can accept an electron pair donated, for example, by a chelating agent.

The term "free coordination site" refers to a coordination site on a metal ion that is occupied by a water molecule or other species that is weakly donating relative to a polyamino acid tag, such as a histidine tag.

The term "coordination number" refers to the number of coordination sites on a metal ion that are available for accepting an electron pair.

The term "coordinate bond" refers to an interaction between an electron pair donor and a coordination site on a metal ion leading to an attractive force between the electron pair donor and the metal ion.

The term "coordination" refers to an interaction in which one multi-electron pair donor, such as a chelating agent or a polyamino acid tag acting as a chelating agent, coordinatively bonds (is "coordinated") to one metal ion with a degree of stability great enough that an interaction that relies upon such coordination for detection can be determined by a biosensor. The metal ion is coordinated by the multi-electron pair donor.

The term "solid phase" refers to any material insoluble in a medium containing a target molecule or biological molecule that is desirably captured in accordance with the invention. This term can refer to a metal film, optionally provided on a substrate.

The term "surface" refers to the outermost accessible molecular domain of a solid phase.

The term "capturing" refers to the analysis, recovery, detection, or other qualitative or quantitative determination of an analyte in a particular medium. The medium is generally fluid, typically aqueous. The term, "captured", refers to a state of being removed from a medium onto a surface.

The term "target molecule" refers to a molecule, present in a medium, which is the object of attempted capture.

The term "determining" refers to quantitative or qualitative analysis of a species via, for example, spectroscopy, ellipsometry, piezoelectric measurement, immunoassay, and the like.

The term "immobilized", used with respect to a species, refers to a condition in which the species is attached to a surface with an attractive force stronger than attractive forces that are present in the intended environment of use of the surface and that act on the species, for example solvating and turbulent forces. Coordinate and covalent bonds are representative of attractive forces stronger than typical environmental forces. For example, a chelating agent immobilized at a surface, the surface being used to capture a biological molecule from a fluid medium, is attracted to the surface with a force stronger than forces acting on the chelating agent in the fluid medium, for example solvating and turbulent forces.

The term "non-specific binding" (NSB) refers to interaction between any species, present in a medium from which a target or biological molecule is desirably captured, and a binding partner or other species immobilized at a surface, other than desired biological binding between the biological molecule and the binding partner.

The term "self-assembled monolayer" refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis, P. E.; Hickman, J.; Wrighton, M. S.; Whitesides, G. M. *Science* 245, 845 (1989), Bain, C.; Evall, J.; Whitesides, G. M. *J. Am. Chem. Soc.* 111, 7155–7164 (1989), Bain, C.; Whitesides, G. M. *J. Am. Chem. Soc.* 111, 7164–7175 (1989), each of which is incorporated herein by reference.

The term "self-assembled mixed monolayer" refers to a heterogeneous self-assembled monolayer, that is, one made up of a relatively ordered assembly of at least two different molecules.

SUMMARY OF THE INVENTION

The foregoing and other objects and advantages of the invention are achieved by providing a molecule having a formula X—R—Ch, in which X represents a functional group that adheres to surface such as a gold surface, R represents a spacer moiety that promotes formation of a self-assembled monolayer of a plurality of the molecules, and Ch represents a bidentate, tridentate, or quadradentate chelating agent that coordinates a metal ion. The chelating agent includes a chelating moiety and a non-chelating linker moiety, such that it can be covalently linked via its linker moiety to the spacer moiety while allowing the chelating moiety to coordinate a metal ion. According to a preferred aspect of the invention a metal ion is coordinated to the chelating agent, and a binding partner of a target molecule is coordinated to the metal ion. This arrangement is facilitated by selecting the chelating agent in conjunction with the metal ion such that the chelating agent coordinates the metal ion without completely filling the ion's coordination sites, allowing the binding partner to coordinate the metal ion via coordination sites not filled by the chelating agent. According to one aspect of the invention the binding partner is a biological species that includes a polyamino acid tag, such as a tag made up of at least two histidine residues, that coordinates the metal ion. In this context the term "adhere" means to chemisorb in the manner in which, for example, alkyl thiols chemisorb to gold.

The present invention also provides a species having a formula X—R—Ch—M—BP—BMol, in which X represents a functional group that adheres to a surface, R represents self-assembled monolayer-promoting spacer moiety, Ch represents a chelating agent that coordinates a metal ion, M represents a metal ion coordinated by the chelating agent, BP represents a biological binding partner of a biological molecule, and BMol represents the biological molecule. The binding partner is coordinated to the metal ion.

The invention also provides an article including a solid phase that has a surface. A plurality of chelating agents are immobilized at the surface in such a way that essentially each of the chelating agents is oriented so as that the chelating moiety of the agent, that is the electron donating portions of the agent, face in a direction away from the surface and is unencumbered by species, such as other chelating agents, that would interfere with the chelating function. This can be accomplished by isolating the chelating agent at the surface by non-chelating species. In this way each chelating agent can coordinate a metal ion so as to expose in a direction away from the surface at least two free metal coordination sites. According to one aspect of the invention the article includes a surface and a self-assembled mixed monolayer adhered to the surface and formed of at least a first and a second species. The first species has a formula X—R—Ch, where X, R, and Ch are each selected such that X represents a functional group that adheres to the surface, R represents a spacer moiety that promotes self-assembly of the mixed monolayer, and Ch represents a chelating agent that coordinates a metal ion. The second species is selected to form a mixed self-assembled monolayer with the first species, and the mixed monolayer is made up of at least 70 mol percent of the second species. The second species preferably is a species selected to inhibit non-specific binding of a protein to the surface.

According to a preferred aspect, the article is suitable for capturing a biological molecule. According to this aspect a self-assembled mixed monolayer, formed of a first species and a second species, is adhered to the surface. The first species has a formula X—R—Ch—M—BP, where X, R, Ch, M, and BP are each selected such that X represents a functional group that adheres to the surface, R represents a spacer moiety that promotes self-assembly of the mixed monolayer, Ch represents a chelating agent that coordinates a metal ion, M represents a metal ion, and BP represents a binding partner of the biological molecule. The binding partner is coordinated to the metal ion. The second species is selected to form a mixed, self-assembled monolayer with the first species, and according to a preferred aspect the second species has a formula, X—R—O—(CH$_2$CH$_2$-O)$_n$-H, in which X represents a functional group that adheres to the surface, R represents a spacer moiety that promotes formation of a self-assembled monolayer of a plurality of the molecules, and n is from one to ten. The article can be constructed and arranged to facilitate instrumental determination of an analyte, and according to a preferred aspect is a biosensor element such as a SPR chip.

The present invention also provides a method of making an article for capturing a target molecule. The method of making the article includes formulating a solution containing a mixture of at least a first and a second species, and exposing to the solution a surface of the article for a period of time sufficient to form a self-assembled mixed monolayer of the first and second species on the surface. The first species has a formula X—R—Ch as described above. The second species is selected to form a mixed self-assembled monolayer with the first species, and the second and first species are present in the solution at a molar ratio of at least 70:30.

The present invention also provides a method of capturing a biological molecule. The method involves contacting a medium suspected of containing the biological molecule with a solid phase that has a surface carrying a plurality of binding partners of the biological molecule, in which essentially all of the binding partners are oriented to expose away from the surface a recognition region for the biological molecule. The biological molecule then is allowed to biologically bind to the binding partner, and the biological molecule bound to the binding partner then can be determined. According to one aspect the method involves providing a solid phase having a surface, a chelating agent immobilized at the surface, a metal ion coordinated by the chelating agent, and a biological binding partner of the biological molecule coordinated to the metal ion. According to this aspect the surface is brought into contact with a medium suspected of containing the biological molecule for a period of time sufficient to allow the biological molecule to biologically bind to the binding partner.

The present invention provides another method of capturing a biological molecule. The method involves providing a solid phase having a surface, and a metal ion immobilized at the surface in such a way that the metal ion has at least two free coordination sites. A biological binding partner of a biological molecule is coordinated to the metal ion via a polyamino acid tag, and a medium containing the biological molecule is brought into contact with the surface, whereupon the biological molecule is allowed to biologically bind to the binding partner. The biological molecule then can be determined.

The present invention provides yet another method of capturing a biological molecule. This method involves providing a solid phase that has a surface having adhered thereto a species having a formula X—R—Ch—M—BP, in which X represents a functional group that adheres to the surface, R represents a self-assembled monolayer-promoting spacer moiety, Ch represents a chelating agent that coordinates a metal ion, M represents a metal ion coordinated by the chelating agent, and BP represents a binding partner of the biological molecule, coordinated to the metal ion. A target molecule then is allowed to biologically bind to the binding partner. The biological molecule then can be determined, for example by detecting a physical change associated with the surface.

An article provided in accordance with the invention can be a biosensor element, such as a SPR chip, and the determination carried out by measuring surface plasmon resonance associated with the chip. The methods of the invention that involve capturing a molecule can involve removal of a preselected molecule, such as a biological molecule, from a fluid medium.

The present invention also provides sensing elements fashioned as described above and suitable for use in a biosensor, for determination of a biological molecule and in particular a molecule that is a binding partner of a nucleic acid strand. A particularly preferred sensing element includes a substrate, a metal film having a surface, and a self-assembled monolayer of a species X—R—NA or X—R—NA—NAB. X represents a functional group that adheres to the surface, R represents a spacer moiety that promotes formation of a self-assembled monolayer of a plurality of the species, NA represents a nucleic acid strand, and NAB represents a nucleic acid strand that is a binding partner of NA and a binding partner of the biological molecule to be determined.

The present invention also provides a kit including an article having a surface and a molecule X—R—Ch, both as described above. The kit can include M and BP, either separately or combined as species X—R—Ch—M or X—R—Ch—M—BP, where X, R, Ch, M, and BP are as described herein. The kit also can include X—R—NA, optionally with NAB, or X—R—NA—NAB as described herein.

Another aspect of the invention is the article formed when the foregoing molecule(s) is adhered to a surface, preferably gold.. In this embodiment the article has a chelating agent as described above attached to a spacer moiety as described above which in turn is adhered via X.

In another aspect the invention provides a self-assembled monolayer including a species X—R—Ch as described above, wherein at least 90% of the Ch units are isolated from all other Ch units. In one embodiment, the Ch units are isolated from each other by at least 5 nm. They can be isolated from each other by a biologically-inert self-assembled monolayer-forming species.

In another aspect, the invention provides a self-assembled monolayer-forming species including a nucleic acid strand. The nucleic acid strand can be single-stranded DNA or double-stranded DNA, or another species. The nucleic acid strand can be a single nucleic acid strand free of hybridization from a complementary strand, and/or can form a part of a self-assembled monolayer of other nucleic acid strand species. The nucleic acid strand can be covalently coupled to a self-assembled monolayer-forming species, thereby forming a part of a self-assembled monolayer.

The invention also provides a single nucleic acid strand that is immobilized at a surface, which immobilization can be covalent immobilization, and the strand is not removable from the surface under disassociation conditions and is free of hybridization to any nucleic acid strand not removable from the surface under disassociation conditions. The nucleic acid strand, according to this aspect, can be hybridized to a complementary nucleic acid strand that is disassociable from the single strand under disassociation conditions.

According to another aspect, the invention provides a surface on which is a self-assembled monolayer including a plurality of self-assembled monolayer-forming species each including a nucleic acid strand. At least 90% of the nucleic acid strands are biologically isolated from all other nucleic acid strands in this aspect. At least 90% of the nucleic acid strands are isolated from each other by at least 5 nm according to one embodiment, and can be isolated from each other by a biologically inert self-assembled monolayer-forming species.

According to another aspect, the invention provides a method including providing a single nucleic acid strand immobilized at a surface, and allowing a biological binding partner of the nucleic acid strand to biologically bind to the strand. The single nucleic acid strand can be covalently immobilized to the surface or immobilized in any other way as part of a self-assembled monolayer in preferred embodiments, and preferably is isolated from other single nucleic acid strands as described above. Alternatively, double-stranded nucleic acid can be immobilized at the surface in this way. In one embodiment, the biological binding partner is a nucleic acid strand that is complementary to the nucleic acid strand immobilized at the surface. In another embodiment the binding partner is a protein or the like.

Other advantages, novel features and objects of the invention will become apparent from the following detailed description of the invention when considered in conjunction with the accompanying drawings.

BRIEF DESCRIPTION OF THE DRAWINGS

In the drawings:

FIG. 1 is a SPR sensorgram illustrating response of a prior art chip carrying Gal 11 to SRB2;

FIG. 2 is a SPR sensorgram illustrating response of a chip derivatized in accordance with the present invention, and carrying Gal 11, to SRB2;

FIG. 3 is a SPR sensorgram illustrating response of a prior art chip carrying a T cell receptor (ABC) to monoclonal antibodies C1 and BF1;

FIG. 4 is a SPR sensorgram illustrating response of a chip, derivatized in accordance with the present invention and carrying a T cell receptor (ABC), to monoclonal antibodies C1 and BF1; and FIG. 5 is a SPR sensorgram illustrating response of a chip, derivatized in accordance with the invention to present a single-stranded nucleotide sequence, first to double-stranded DNA carrying a single-stranded "tail" scrambled with respect to that presented by the chip, and then to a single-stranded "tail" complementary to that presented by the chip;

FIG. 6 is a SPR sensorgram illustrating response of the chip of FIG. 5 to double-stranded DNA without a "tail";

FIG. 7 is a SPR sensorgram illustrating response of a chip carrying double-stranded DNA including 2Gal4 binding sites to Gal4 and to LexB17;

FIG. 8 is a schematic illustration of a surface derivatized with a mixed SAM formed of an inert major component and a minor component that includes a nucleic acid strand;

FIG. 9 is a schematic illustration of the SAM of FIG. 8 following hybridization with double-stranded DNA having a "tail" complementary to the nucleic acid strand presented by the surface after hybridization, ligation, and restriction; and FIG. 10 is a schematic illustration of hybridization of double-stranded DNA, ligated with the same restriction enzyme used to ligate the double-stranded DNA immobilized at the surface, to the DNA of the surface followed by ligation and disassociation.

DETAILED DESCRIPTION OF THE INVENTION

U.S. Pat. No. 5,620,850, filed Sep. 26, 1994 by Bamdad, et al., entitled "Molecular Recognition at Surfaces Derivatized with Self-Assembled Monolayers", now pending, is incorporated herein by reference. A commonly owned, co-pending application entitled "Surface-Immobilized Nucleic Acid and Electron Transfer Devices and Methods Employing the Same" of Bamdad, et al., filed on even date herewith, is incorporated herein by reference as well.

The present invention provides, according to one aspect, a method of capturing a biological molecule at a surface, using a biological binding partner of the molecule that is immobilized at the surface. In the case of many biological molecules, biological binding is extremely sensitive to orientation and conformation of the members involved in the binding, that is, the biological molecule and the binding partner. Accordingly, the manner of presentation of the binding partner at the surface to a medium containing the biological molecule is directly related to the sensitivity, and success, of the technique.

Accordingly, one method of the present invention provides a chelating agent immobilized at a surface of a solid phase, a metal ion coordinated by the chelating agent, and a biological binding partner of the biological molecule coordinated to the metal ion. the biological binding partner includes a polyamino acid tag that coordinates the metal ion, and a recognition region for the biological molecule remote from the polyamino acid tag. A medium containing the biological molecule is brought into contact with the surface for a period of time sufficient to allow the biological molecule to biologically bind to the binding partner.

The chelating agent and metal ion are selected such that at least two free coordination sites remain on the metal ion after coordination by the chelating agent, and the chelating agent is oriented so as to expose away from the surface the free coordination sites. It is especially preferred that the at least two free coordination sites of the metal are adjacent to each other. Thus, a biological binding partner that includes both a polyamino acid tag that coordinates the metal ion, and a recognition region for the biological molecule that is remote from the polyamino acid tag, is readily immobilized at the surface by coordination to the ion. In this state the binding partner exposes away from the surface the recognition region. In accordance with the method, superior biological binding is observed between a biological molecule in a medium contacted with the surface, and the surface-immobilized binding partner.

The present invention provides an article that can facilitate the above and other methods of the invention. The article includes a solid phase having a surface and a self-assembled mixed monolayer adhered to the surface, the mixed monolayer formed of at least a first species and a second species. The first species has a formula X—R—Ch, in which X, R, and Ch are each selected such that X represents a functional group that adheres to the surface, R represents a spacer moiety that promotes self-assembly of the mixed monolayer, and Ch represents a chelating agent that coordinates a metal ion. The second species is selected to form a mixed self-assembled monolayer with the first species, and the molar ratio of the second to the first species is at least 70:30. According to a preferred embodiment, the molar ratio is at least 80:20, according to a more preferred embodiment the molar ratio is at least 90:10, and according to a particularly preferred embodiment, the mixed monolayer is made up of about 95 mol % of the second species and about 5 mol % of the first species. A variety of spectroscopic techniques are available to those of ordinary skill in the art for determining a final ratio of first and second species immobilized at a surface.

According to an aspect of the invention particularly useful in the above-described and other articles and methods, a metal ion is coordinated to the chelating agent, and the metal ion and chelating agent are selected so that at least two coordination sites of the metal remain free after coordination by the chelating agent. One embodiment of this aspect of the invention is facilitated by the above-described molar ratio of the second to the first species of the invention, as discussed below.

A mixed monolayer of the first and second species in the molar ratio of the invention is important to the superior sensitivity of the article. The molar ratio provides for isolation of each chelating agent immobilized at the surface. That is, each chelating agent is separated from other chelating agents by a distance sufficient to assure that each metal ion presented to the surface is coordinated by one chelating agent only, rather than being tethered by coordinate bonds to two or more chelating agents. This is important for several reasons, including the following. When each metal ion is coordinated by one chelating agent, the number of free coordination sites on the metal available for further coordinate bonding is controlled. That is, selection of a chelating agent and a metal ion can be made in such a manner that the ratio of chelating agents to metal ions at the surface is essentially 1:1, and a desired number of free coordination sites exist on each metal after coordination by the chelating agent. In contrast, if chelating agents are present at the surface in sufficient proximity to each other such that more than one chelating agent can form coordinate bonds with a single metal ion, the metal ion can be coordinated at more than a desired number of coordination sites by the multiple chelating agents, leaving less than a desired number of free coordination site for further coordinate bonding. Additionally, in such a situation control over orientation of the any free coordination sites on the metal ion can be lost; free coordination sites may not face away from the surface, but may face in a direction inaccessible by a species desirably subsequently coordinated to the metal ion at the surface. Further, in such a situation in which a chelating agent can form a coordinate bond with more than one metal ion, one or more electron pairs of a chelating agent available for donation can remain uninvolved in coordinate bonding, which can lead to NSB at the surface. In short, the molar ratio of the second to the first species provides control such that the metal ion is coordinated as stably as possible (lowest possible energy state between chelating agents and metal ions), is oriented with free coordination sites facing away from the surface, and NSB at the surface is minimized or eliminated.

According to one aspect of the invention, the second species is selected to expose to the medium containing the biological molecule a functionality that inhibits NSB. Specifically, a functionality is selected to inhibit NSB of species present at relatively high concentration in a medium in which the biological molecule is presented to the surface. That is, the second species is selected among those that include chemical functionality, at the end of the molecule opposite the functionality that adheres to the surface, that does not bind species in the medium (the end opposite the functionality that adheres to the surface is presented to the medium, or "exposed" at the surface).

The second species has a formula X—R—NSBi, where NSBi is a NSB-inhibitor. NSBi can be selected from such groups as $—CH_3$; $—OH$; $—O(CH_2)_nH$, where n=1–15, preferably 1–7; $—CONH(CH_2)_nH$, where n=1–15, preferably 1–7; $—NHCO(CH_2)_nH$, where n=1–15, preferably 1–7; $—(OCH_2CH_2)_nH$, where n=1–15, preferably 1–7; $—COOH$; $—O(CH_2CH_2—O)_nH$ (where n=1–10); $—(CF_2)_nCF_3$, where n=1–20, preferably 1–8; olefins, and the like.

Preferred are —CH$_3$, —OH, and —O(CH$_2$CH$_2$—O)$_n$H. According to a preferred embodiment in which a medium containing biological, particularly proteinaceous, species contacts the surface, the second species preferably has a formula X—R—O—(CH$_2$CH$_2$—O)$_n$-H, in which X represents a functional group that adheres to the surface, R represents a spacer moiety that promotes formation of a self-assembled monolayer of a plurality of the molecules, and n is from one to ten. According to a more preferred embodiment, n is from 2 to 5, and according to a particularly preferred embodiment, n is 3.

The surface, and the functional group X that adheres to the surface, can be selected among a wide variety known to those of skill in the field of surface science. A nonlimiting exemplary list of combinations of surface materials and functional groups X suitable for use in the present invention follows. Although the following list categorizes certain preferred materials with certain preferred functional groups which firmly bind thereto, many of the following functional groups would be suitable for use with exemplary materials with which they are not categorized, and any and all such combinations are within the scope of the present invention. Preferred surface materials include metals such as gold, silver, copper, cadmium, zinc, palladium, platinum, mercury, lead, iron, chromium, manganese, tungsten, and any alloys of the above with sulfer-containing functional groups X such as thiols, sulfides, disulfides, and the like; doped or undoped silicon with silanes and chlorosilanes; metal oxides such as silica, alumina, quartz, glass, and the like with carboxylic acids; platinum and palladium with nitriles and isonitriles; and copper with hydroxamic acids. Additional suitable functional groups include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as a surface material in the present invention. Additional materials and functional groups suitable for use in the present invention can be found in U.S. Pat. No. 5,079,600, issued Jan. 7, 1992, incorporated herein by reference.

According to a more preferred embodiment, a combination of gold as surface material and a functional group X having at least one sulfer-containing functional group such as a thiol, sulfide, or disulfide is selected. The interaction between gold and such sulfer-containing functional groups is a well-studied science, and a nonlimiting representative exemplary list of such sulfer-containing functionalities may be found in an article entitled "Wet Chemical Approaches to the Characterization of Organic Surfaces: Self-Assembled Monolayers, Wetting and the Physical-Organic Chemistry of the Solid-Liquid Interface", by G. W. Whitesides and Paul E. Laibinis, Langmuir, 6, 87 (1990), incorporated herein by reference. Particularly preferred in the present invention is a gold surface, and a thiol as functional group X.

The spacer moiety R can be selected from among organic spacer moieties that promote formation of self-assembled monolayers. Such moieties are well-known to those of ordinary skill in the art, as described in the above-referenced articles by Laibinis, et al. *Science* 245, 845 (1989), Bain, et al. *J. Am. Chem. Soc.* 111, 7155–7164 (1989), and Bain, C, et al. *J. Am. Chem. Soc.* 111, 7164–7175 (1989). Preferred moieties R are hydrocarbon chains optionally interrupted by hetero groups, of a length of at least eight carbon atoms. As used herein, "hydrocarbon" is meant to define includes alkyl, alkenyl, alkynyl, cycloalkyl, aryl, alkaryl, aralkyl, and the like. Hetero groups can include —O—, —CONH—, —CONHCO—, —NH—, —CSNH—, —CO—, —CS—, —S—, —SO—, —(OCH$_2$CH$_2$)$_n$R (where n=1–20, preferably 1–8), —(CF$_2$)$_n$- (where n=1–20, preferably 1–3), olefins, and the like. It is important that the R is a self-assembled monolayer-promoting moiety. Whether or not a particular moiety promotes formation of a self-assembled monolayer can be routinely determined by one of ordinary skill in the art, optionally in accordance with the teachings of the preceding references, using for example surface spectroscopic techniques.

According to a preferred embodiment, R=—(CH$_2$)$_n$-, where n is from about 8 to about 24, preferably from about 10 to about 20, most preferably from about 9 to about 16. According to an embodiment of the invention in which R is a moiety in the group X—R—Ch, R preferably comprises —(CH$_2$)$_n$-O(CH$_2$CH$_2$—O)$_m$-, where n=4–20, preferably 8–14, and m=1–10, preferably 2–5. a variety of moieties R can be used on different molecules forming a self-assembled mixed monolayer, so long as other requirements described herein are met.

R should also be selected to be chemically stable to reagents used in the synthesis of a species into which it is incorporated. For example, if the species is formed by cleavage of a disulfide, R should be stable to reagents such as mercaptoethanol and dithiothreitol.

The metal ion is preferably selected from those that have at least four coordination sites, preferably six coordination sites. a non-limiting list of metal ions suitable includes Co$^{3+}$, Cr$^{3+}$, Hg$^{2+}$, Pd$^{2+}$, Pt$^{2+}$, Pd$^{4+}$, Pt$^{4+}$, Rh$^{3+}$, Ir$^{3+}$, Ru$^{3+}$, Co$^{2+}$, Ni$^{2+}$, Cu$^{2+}$, Zn$^{2+}$, Cd$^{2+}$, Pb$^{2+}$, Mn$^{2+}$, Fe$^{3+}$, Fe$^{2+}$, Au$^{3+}$, Au$^+$, Ag$^+$, Cu$^+$, MO$_2^{2+}$, Tl$^{3+}$, Tl$^+$, Bi$^{3+}$, CH$_3$Hg$^+$, Al$^{+3}$, Ga$^{3+}$, Ce$^{3+}$, UO$_2^{2+}$, and La$^{3+}$.

The chelating agent is preferably selected from bidentate, tridentate, and quadradentate chelating agents, and is selected in conjunction with the metal ion so that when the chelating agent coordinates the metal ion, at least two free coordination sites of the metal remain. The chelating agent and metal are selected so that the chelating agent can coordinate the metal ion with a degree of stability great enough that the metal ion will remain immobilized at the surface by the chelating agent.

Additionally, the chelating agent is selected as one that has a chelating moiety and a non-chelating linker moiety, such that it can be covalently linked via its linker moiety to the spacer moiety R while leaving the chelating moiety undisturbed by the covalent linkage and free to coordinate a metal ion. Alternatively, the chelating agent can be selected as one that can be modified via routine organic synthesis to include a non-chelating linker moiety, if such synthesis leaves undisturbed the chelating moiety. One of ordinary skill in the art will appreciate that the non-chelating linker moiety should provide functionality suitable for chemical linkage such as, for example, an amine, alcohol, carbamate, carboxylic acid, thiol, aldehyde, olefin, etc., for formation of an ester linkage, formation of an amide linkage, thiol displacement and this ether formation, and the like.

With the above considerations in mind, suitable chelating agents and corresponding metal ions can be selected by those of ordinary skill in the art. In accordance with such selection reference can be made to "Chelating Agents and Metal Chelates", Dwyer, F. P.; Mellor, D. P., Academic Press, and "Critical Stability Constants", Martell, a. E.; Smith, R. M., Plenum Press, New York. These works describe a variety of chelating agents, and discuss the stability of coordination between chelating agents and metal ions. Preferably, a chelating agent and metal ion is selected such that the disassociation constant of the combination in aqueous solution is better than 10 nM at physiological pH, that is, such that at least one half of the metal ions are coordinated by chelating agent at a concentration of 10 nM.

a non-limiting exemplary list of suitable chelating agents includes nitrilotriacetic acid, 2,2'-bis(salicylideneamino)-6,6'-demethyldiphenyl, and 1,8-bis(a-pyridyl)-3,6-dithiaoctane.

In some cases it may be advantageous to test a particular chelating agent/metal ion pair to determine whether coordination will be sufficiently stable for use in the present invention. It is within the realm of routine experimentation to one of ordinary skill in the art to follow the teachings herein to immobilize a chelating agent at a surface, such as at a gold SPR chip surface, and then to test the interaction between the chelating agent and the metal ion via, for example, SPR spectroscopy under various conditions. In addition, preliminary screening can be carried out by reacting a prospective chelating agent and metal ion in solution and analyzing the solution spectroscopically. In this regard, reference can be made to, "Spectroscopy and Structure of Metal Chelate Compounds", Nakamoto, K.; McCarthy, S. J., Wiley, New York.

According to one aspect of the invention, an article suitable for capturing a biological molecule is provided. The article includes a self-assembled mixed monolayer of a first species and the second species as described above. The first species has a formula X—R—Ch—M—BP, where X, R, Ch, and M are as described above, and BP is a binding partner of a biological molecule, coordinated to the metal ion.

According to a preferred embodiment the binding partner includes a recognition region for the biological molecule, and a polyamino acid tag that can coordinate the metal ion and that is remote from the recognition region. a polyamino acid tag is meant to define a series of amino acids in proximity such that they can coordinate the at least two free coordination sites of the metal ion. According to a one embodiment, from 2 to about 10 neighboring amino acids such as, for example, neighboring histidines, lysines, arganines, glutamines, or any combination of these can serve as a polyamino acid tag. According to a preferred embodiment, the polyamino acid tag includes at least two, and more preferably from two to 10 neighboring histidines, and according to a particularly preferred embodiment the polyamino acid tag includes from about 3 to about 8 neighboring histidines. With reference to the above-identified work entitled, "Critical Stability Constants" (Martell, et al), selection of these and additional amino acids can be made in conjunction with selection of a metal ion M.

A variety of vectors that express proteins or fragments thereof containing a histidine tag are commercially available from, for example, Novagen, of Madison, Wis. However, these vectors are designed to code proteins or fragments for metal chelate affinity chromatography. For purposes of metal chelate affinity chromatography, it is not important where on the vector the histidine tag lies. The purpose of the histidine tag in that application is solely to allow the chromatography solid phase to adsorb the protein. Therefore, it is not a priority in the commercialization of histidine-tagged proteins that the tag be placed at a location remote from the recognition region.

Where the binding partner is a polyamino acid, a polyamino acid tag can be expressed at a desired location (remote from the recognition region) in a number of ways known to those of ordinary skill in the art, for example by employing the polymerase chain reaction (PCR) to incorporate a nucleic acid sequence that encodes the polyamino acid tag at the appropriate position. Placement of a polyamino acid tag at a desired location is discussed more fully below.

Modification of a protein or fragment thereof by applying to the protein or fragment a polyamino acid tag at a location remote from the recognition region of the protein or fragment can be accomplished readily by one of ordinary skill in the art using, for example, recombinant technology. According to one method for such modification, a desired protein is grown from DNA that codes for the protein, and an expression vector. The protein is isolated and truncated at various amino acid positions, and the protein's specific active sequence (recognition region) elucidated by randomly mutating the resultant sequences. Alternatively, via sequence homology, a variety of similar proteins that recognize slightly different species are identified and their amino acid sequences determined. The various sequences are compared using a computer, and regions that are variable between the various proteins identified as recognition regions.

Subsequently a strand of DNA for a the desired protein fragment that is large enough to correctly fold can be sequenced with a polyamino acid tag at a location remote from the recognition region. DNA sequencing is routine in the art via, for example, PCR. With an expression vector, the desired polyamino acid-tagged protein fragment then can be readily grown and isolated.

The desired fragment will coordinate to the metal ion via the polyamino acid tag, and the recognition region, remote from the tag, will not face the surface, but will be exposed to the medium containing or suspected of containing the binding partner of the protein fragment. As used herein, the term "remote" is meant to define a situation in which the polyamino acid tag is separated from the recognition region by a distance of at least about 20 amino acids, preferably at least about 40 amino acids.

The polyamino acid tagging technique of the invention can be applied to a variety of polyamino acids such as proteins, antibodies, antigens, polymers, and ligands.

Where the binding partner is a not a polyamino acid, it can be coupled chemically, for example covalently coupled, to a polyamino acid including a polyamino acid tag. In this case the coupling of the polyamino acid is effected on the binding partner at a location remote from the recognition region, and/or the polyamino acid that is coupled to the binding partner has a tag at a location remote from the location of coupling to the binding partner. Synthesis of such a species would be routine to those of ordinary skill in the art.

The present invention also provides a method of making an article having a surface for capturing a target molecule. The method involves formulating a solution containing a mixture of at least the first and second self-assembled monolayer-forming species above, and exposing to the surface the solution for a period of time sufficient to form a self-assembled monolayer on the surface.

The amount of time required to allow the monolayer to spontaneously chemisorb to the surface will vary depending upon the solvent, the surface, and the monolayer-forming species. Typically, the time required will be on the order of hours, and often a 24-hour exposure is carried out to make certain that maximal coverage is obtained. The degree of formation of a monolayer can be determined by routine spectroscopic methods, as well as physical method in some cases, such as contact angle measurements and the like.

Other methods for forming the monolayer on the surface are included, for example those disclosed in U.S. Pat. No.

5,512,131, filed Oct. 4, 1994 and entitled, "Formation of Microstamped Patterns on Surfaces and Derivative Articles", incorporated herein by reference.

The present invention also provides a SAM-forming species that includes, at least in part, a nucleic acid strand, and can include double-stranded nucleic acid. The SAM-forming species according to this aspect of the invention when defining, in part, a SAM on a surface of an article, can define a sensing element suitable for use in a biosensor, and especially for use in determining a binding partner of a nucleic acid strand.

It has become evident that substances that interact when one or more are bound to DNA do so in a manner that can be highly dependent on the presence of the DNA. Therefore, detailed studies of intricate and sometimes delicate interactions require the presence of the cognate DNA site(s). One example is the study of the interactions which occur in the regulation of transcription. This work is critical for the understanding of many diseases, such as cancer and AIDS. Another example is in the study the interactions of glycoproteins, other saccharides, nucleic acid materials, and potential drugs with their intended DNA target(s). Existing methods for the study of protein/DNA interactions, and other interactions that are best studied with surface-bound DNA, typically require that biotinylated DNA be bound to streptavidin coupled to a dextran surface. Concerns regarding this technique, as practiced in the prior art, include: 1) the net negative surface charge may mimic DNA electrostatic affects leading to significant amounts of non-specific binding and incorrect kinetic measurements; 2) the thickness of the dextran, a layer of streptavidin, biotin, plus the length of the DNA, may put the interaction out of the distance range where SPR measurements can be reliably done; 3) the resrictive DNA size limitation of synthetically produced DNA (50–75 bps) and the high expenses incurred by using commercial biotinylated DNA severely limits the range of possible experiments.

Accordingly, the invention provides, in one embodiment, a species X—R—NA, or X—R—NA—NAB, as defined below. In another embodiment the invention provides a sensing element including a substrate and a self-assembled monolayer of a species X—R—NA, or X—R—NA—NAB, adhered to the surface of the substrate. The SAM contains, in preferred embodiments, one of these species in combination with an inert, non-binding thiol as discussed above in combination with the species X—R—Ch, etc. The substrate preferably includes a metal surface, such as can be provided by a film of metal on a non-metal substrate. In this set of embodiments, X represents a functional group that adheres to the surface, R represents a spacer moiety that promotes formation of a self-assembled monolayer of a plurality of the species, NA represents a nucleic acid strand, and NAB represents a nucleic acid strand that is a binding partner of NA. NA or NAB can be a binding partner of a biological molecule to be determined.

Referring now to FIGS. 8–10, SAMs including the species X—R—NA and X—R—NA—NAB are illustrated schematically. A description of this aspect of the invention is provided in greater detail below in Examples 10–14, and a brief description is provided here.

Referring to FIG. 8, an article 20 is illustrated which can define an SPR chip in one embodiment. Article 20 includes a substrate 22 having a surface 24 upon which is provided a SAM. In the embodiment illustrated, substrate 22 includes a film 26 on a surface thereof, the exposed surface of film 26 defining surface 24 of the overall substrate arrangement. Where an SPR chip is provided, substrates 22 can be glass and film 26 can be a thin gold film. A SAM 28 is provided on surface 24 of the substrate and includes a major component species 30 and a minor component species 32 which is a SAM-forming species including a nucleic acid strand 34. Nucleic acid strand 34 is preferably covalently coupled to a self-assembled monolayer-forming species X—R which forms a self-assembled monolayer with minor component 30. Minor component 30 is selected to have the ability to form an SAM with nucleic acid strand SAM-forming species 32, is preferably of a length short enough, relative to species 32, that nucleic acid strand 34 of species 32 is exposed for hybridization, and otherwise can include a chemical functionality, exposed away from surface 24, that is desirable for whatever purpose article 20 serves. Typically, minor component 30 will include an NSB-minimizing species such as a species terminating in polyethylene glycol. Synthesis of species 30 and species 32 is described below in the examples. The mixed monolayer including species 30 and species 32 includes nucleic acid strands 34 that are biologically isolated from all other nucleic acid strands. In particular, at least 90% of nucleic acid strands 34 are biologically isolated from other nucleic acid strands. As used herein, the term "biologically isolated" is meant to define a situation in which, were the nucleic acid strands complementary to each other, they would hybridize or interact in another way. "Biologically-isolated" is also meant to define a situation in which if one nucleic acid strand included a region specific for a protein, and a protein were immobilized at that strand, if a neighboring nucleic acid strand had a sequence for that protein, the protein would not interact biologically (via biological binding or other recognition) with that strand. Specifically, at least 90% of nucleic acid strands 34 are isolated from all other nucleic acid strands, preferably by inert SAM-forming species 30, by at least 5 nm.

Article 20 can be used for a variety of purposes in which it: is advantageous to expose a single-stranded nucleotide at a surface. In one preferred embodiment, with reference to FIG. 9, double-stranded nucleic acid (e.g. double-stranded DNA, dsDNA, as referred to hereinafter) 36, one of the strands having a "tail" 38 that is complementary to nucleic acid strand 34 covalently immobilized at surface 24, is exposed to the surface and dsDNA 36 hybridizes to strand 34 via tail 38.

Thus, a single nucleic acid strand is provided that can be covalently linked to surface 24. As used herein, "covalently" is meant to define linkage that is stronger, chemically, than non-covalent linkage such as Van der Waals interactions, ionic interactions, coordinate bonding, and the like. Linkage of species such as X at an appropriate surface, for example thiol linkage to gold, is covalent. The use of component 30 allows nucleic acid strands 34 to be presented at the surface while free of interaction with any neighboring nucleic acid strands. This allows freer access to binding, recognition, and other interaction.

The "nick" 40 in the nucleic acid strand can be mended with DNA ligase enzyme, resulting in immobilized dsDNA species 42 covalently attached to surface 24 via strand 44 extended in the course of the hybridization/ligating step described. When the dsDNA is selected to contain a restriction enzyme site, a restriction enzyme 46 can be used to cut the dsDNA 42. Referring now to FIG. 10, the resulting cut, surface-immobilized dsDNA species 48 can be ligated with any dsDNA that has been cut also with restriction enzyme 46. As illustrated, dsDNA 50 can be hybridized to species 48 and the "nicks" mended with DNA ligase, resulting in surface-immobilized, dsDNA 52 including covalently-immobilized strand 54 and strand 56 which is immobilized via hybridization to strand 54. The "antisense" strand 56 can be dissociated with heat or chemical treatment to expose ssDNA 54 for hybridization studies. Of course, in FIG. 10 strands 54 and 56 include nucleic acids that are not represented throughout the length of each strand.

Thus, the embodiment of the invention represented in FIGS. 8–10 includes a single nucleic acid strand immobilized, preferably covalently immobilized, at a surface and not removable from the surface under disassociation conditions. As used herein, the term "disassociation conditions" is meant to define a situation in which, where a single strand 54 is covalently immobilized at the surface and a complementary strand 56 is hybridized to strand 54, strand 56 can be removed. These conditions include hot water, mild chemical treatment, and other techniques available to those of ordinary skill in the art. The invention also includes single strand 54 immobilized to the surface and not removable therefrom under disassociation conditions, and complementary strand 56 hybridized to strand 54 and removable from the surface under disassociation conditions.

Single-stranded or double-stranded nucleic acid can be used to bind, at the surface, biological binding partners that are partners of the immobilized strand or strands, and used in further study. For example, a binding partner of an immobilized strand or strand can be immobilized at the surface, and can serve as a binding partner of yet another biological binding partner that then is immobilized, and that species used in studies.

Attachment of a wide variety of nucleic acid strands NA to a moiety R, for example in a way that the strand can biologically bind to its nucleic acid binding partner NAB, can be accomplished with reference to the teaching of examples 10–14, below. It is to be understood that the procedure given in the examples for the preparation of a DNA chip may be applied to the preparation of any nucleic acid chip, such as an RNA chip. Such a chip can be used to detect DNA hybridization (human genome project, diagnostic scanning of DNA for genetic mutants), to present DNA-binding proteins for the study of subsequent protein-protein interactions for which DNA binding is a critical element of the interaction, using instruments such as SPR devices, or to build an easy analysis DNA computer.

The articles of the present invention can be used for a variety of applications, including biosensing applications, test assays, and the like. The term "test assay" generally refers to any procedure in which a member of a biological binding partner pair is to be captured from a medium in which it is dispersed. For example, "test assay" may be used to describe a diagnostic procedure, analytical procedure, microanalytical procedure, forensic analysis, pharmacokinetic study, cell sorting procedure, affinity chromatogram, industrial or laboratory recovery or analysis of one or more species such as toxins, catalysts, or starting materials or products, and the like a typical test assay is an immunoassay. Biosensing applications include those such as drug screening, environmental monitoring, medical diagnostics, quality control in the pharmaceutical and food industries, and other areas in which it is advantageous to sensitively determine biological binding between partners.

One particularly suitable application for the species X—R—NA or X—R—NAB, and a chip carrying a SAM of one or more of these, is the study of interacting proteins and protein-DNA complexes that regulate gene transcription. Large soluble yeast PolII holoenzyme/mediator complexes must communicate with some other DNA-bound complex to effect transcription. Precise and accurate determination of interactions of these large complexes with DNA-bound transcription factors would be advantageous, and can be accomplished with the technique of the present invention.

In accordance with an embodiment of the invention in which an article has a surface with a monolayer of X—R—Ch-M adhered thereto, M can serve as a binding partner to capture species that adhere to M. An exemplary list of such species is disclosed in U.S. Pat. No. 5,250,188, issued Oct. 5, 1993 to Bruening, et al. and incorporated herein by reference.

In all of the embodiments of the invention in which an article is provided, a substrate also may be included in the article. The substrate typically will support a film of material that defines the surface, on a side of the film opposite the side at which a self-assembled monolayer is formed.

The function and advantage of these and other embodiments of the present invention will be more fully understood from the examples below. The following examples are intended to illustrate the benefits of the present invention, but do not exemplify the full scope of the invention. References cited in the following examples are incorporated herein by reference for all purposes.

Example 1: Preparation of Nitrilotriacetic Acid Chelate Linked Via Spacer Moiety To Thiol Undec-1-en-11-yl tri(ethyleneglycol) (1) was synthesized according to a procedure reported by Pale-Grosdemange, C.; Simon, E. S.; Prime, K. L; Whitesides, G. M. *Journal of the American Chemical Society,* 113, 12, (1991).

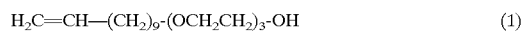

N-(5-amino-1-carboxypentyl)iminodiacetic acid (2) was synthesized according to a procedure reported by Hochuli, E.; Döbeli, H.; Schacher, a. *Journal of Chromatography,* 411, 177 (1987).

Carbonyldiimidizole (2.3 g, 2 eq. was added to a stirring solution of 2.2 g of alcohol (1) dissolved in 25 ml methylene chloride. After stirring for 2 hours, the solution was applied to a 300 g column of silica equilibrated with ethyl acetate and the imidazole carbamate eluted with 1 liter of ethyl acetate. Evaporation of the solvent under reduced pressure gave 2.7 g (95%) of the imidazole carbamate as an oil.

Amine (2) (5.0 g) was dissolved in 100 ml of water. The pH was titrated to 10.2 with 12 N NaOH, then 130 ml of dimethylformamide was added. The imidazole carbamate (2.5 g in 10 ml dimethylformamide) then was added dropwise to aqueous solution of (2) while stirring. After 12 hours, the solution was added to 500 ml water and washed three times with ethyl acetate by gently stirring to avoid the formation of an emulsion The aqueous phase then was acidified with 6 N HCl to pH 1.5 and extracted into ethyl acetate (4×250 ml). The combined extracts were washed with saturated NaCl, dried over $MgSO_4$, and the solvent removed under reduced pressure to give 1.8 g (50%) of olefin (3) as a hydroscopic white solid.

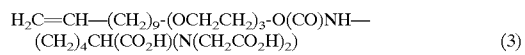

To olefin (3) (1.7 g) dissolved in 15 ml distilled tetrahydrofuran was added 0.5 ml thiolacetic acid and 100 mg 2,2'-azobis(2-methylpropionitrile) (AIBN). The solution was irradiated for four hours under a 450 W medium pressure mercury lamp (Ace Glass). The solvent was removed under reduced pressure and the crude product triturated with hexane. Recrystalization from ethyl acetate/hexane gave 1.8 g (94%) of thioacetate as a hydroscopic tan solid (4).

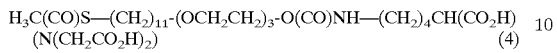

$$H_3C(CO)S-(CH_2)_{11}-(OCH_2CH_2)_3-O(CO)NH-(CH_2)_4CH(CO_2H)$$
$$(N(CH_2CO_2H)_2) \quad (4)$$

To thioacetate (4) (0.67 g). in 20 ml dimethoxyethane was added 17 ml water, then 20 mg $I_2$. After the addition of 3 ml of 2 N NaOH, the solution was stirred for four hours while bubbling with $O_2$. Addition of 100 ml of water and acidification to pH 1.5 with 6N HCl lead to precipitation of the product as the disulfide. The disulfide was filtered, washed with water and dried under vacuum to give 0.55 g (89%) of a white powder.

The disulfide was reduced to the thiol (6) with triethylphosphine. To the disulfide (0.42 g) in 18 ml methanol plus 2 ml water under an atmosphere of nitrogen, was added 0.3 g of triethylphosphine. The solution was stirred for five hours then concentrated to an oil under reduced pressure. The residue was dissolved in 30 ml degassed water and acidified to pH 1.5 with 6N HCl. The product was extracted three times with 20 ml ethyl acetate. The combined organic phases were washed with saturated NaCl, dried over $MgSO_4$, and concentrated under reduced pressure to thiol-linked nitrilotriacetic acid chelate (5) as a tan hydroscopic solid (0.24 g, 57%).

$$HS-(CH_2)_{11}-(OCH_2CH_2)_3-O(CO)NH-(CH_2)_4-$$
$$CH(CO_2H)(N(CH_2CO_2H)_2) \quad (5)$$

Example 2: Preparation of SPR Chip Derivatized With Self-Assembled Mixed Monolayer of Chelate And Nonspecific Binding Inhibitor 11-mercaptoundec-1yl oligo(ethyleneglycol) (6) was synthesized according to a procedure reported by Pale-Grosdemange, et al., *JACS* (1991; above).

$$HS-(CH_2)_{11}-(OCH_2CH_2)_n-OH \quad (6)$$

The gold surface of an SPR chip from Pharmacia Biosensor, Piscataway, N.J. was cleaned using 70:30 $H_2SO_4/H_2O$ to remove all species on the gold. 11-mercaptoundec-1yl oligo(ethyleneglycol) (6) and the thiol-linked nitrilotriacetic acid chelate (5) described in example 1 were dissolved in ethanol in a 95:5 molar ratio, at a total concentration of 1 mM. The chip surface was exposed to the 1 mM solution of the thiols in ethanol for 24 hours, then washed with 95% ethanol and allowed to dry. The derivatized surface was characterized by X-ray photoelectron spectroscopy, which revealed that a mixed monolayer had adhered to the surface, the mixed monolayer including a ratio of (6) and (5) approximately equal to the concentration of those species in the solution from which the surface was derivatized (95:5 molar ratio of (6) to (5)).

Example 3: Incorporation of Metal Cation Into Chelate of Self-Assembled Monolayer on SPR Chip The surface derivatized as described in example 2 to have adhered a self-assembled mixed monolayer formed of a 95:5 molar ratio of species (6) and (5) was further modified to allow the chelate to coordinate nickel dication ($Ni^{2+}$). The mixed monolayer was washed with 1 mM aqueous NaOH followed by 1% aqueous Ni $(SO_4).6H_2O$, resulting in species (5) coordinating $Ni^{2+}$ to define species (7).

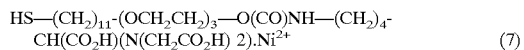

$$HS-(CH_2)_{11}-(OCH_2CH_2)_3-O(CO)NH-(CH_2)_4-$$
$$CH(CO_2H)(N(CH_2CO_2H) 2).Ni^{2+} \quad (7)$$

Example 4: Coordination of Biological Binding Partner To Metal Cation

Gal 11 has been identified as a protein required for efficient galactose utilization in yeast. Nogi, Y.; Fukasawa, T. *Curr. Genet.* 2, 115–120 (1980). Gal 11p (potentiator) is a 44 kD mutant of Gal 11, differing from Gal 11 at a single amino acid only Id. Gal 11 is a suspected biological binding partner of Gal 4 (see discussion in example 5) . a "mini" form of Gal 1ip was expressed and purified (residues 261–351+799–1081) with a polyamino acid tag at a location remote from the recognition region of the protein fragment. Specifically, a run of six histidines is expressed at the amino terminus of the protein fragment, and the histidine-tagged Gal 1ip was isolated out of cell extracts by absorption on a column containing nickel dication coordinated to a nitrilotriacetic acid derivative. Hochuli, et al. *J. Chromatog.* 411, 177 (1987), Gentz, R.; Chen, C.; Rosen, C. a.; *Proc. Natl. Acad. Sci.* 86, 821 (1989).

The polyamino acid-tagged binding partner was attached selectively to the derivatized surface described in example 3 by coordination to the metal cation via the histidine tag. specifically, a 0.25 mg/ml aqueous solution of Gal 11p was injected into a delivery channel of a BIAcore™ SPR instrument, Pharmacia Biosensor. The result was a surface carrying a plurality of binding partners (Gal 11p) oriented such that a substantial portion of the recognition regions for Gal 4 face away from the chip surface and are readily available for biological binding with the biological molecule Gal 4.

Example 5: SPR Determination of Gal 4 Using Chip Derivatized With Self-Assembled Monolayer of Alkyl Thiol Terminating In Metal Chelate Coordinated By Polyamino Acid-Tagged Gal 11p This example examines the sensitivity of the SPR technique for the analysis of the interaction between biological binding partners, with use of an SPR chip prepared in accordance with the present invention. Specifically, the interaction between the transcription promoter Gal 4 and Gal 11p (which contains increased area of hydrophobicity relative to Gal 11), was studied, using a BIAcore™ SPR instrument available from Pharmacia Biosensor, Piscataway, N.J.

It has been reported that in cells deleted for Gal 11, activation by Gal 4 is reduced some 5–20 fold, an effect that can not be accounted for by decreased levels of the activator. Id, Himmelfarb, H. J.; Pearlberg, J.; Last, D. H.; Ptashne, M. *Cell* 63, 1299–1309 (1990), Suzuki, Y.; Nogi, Y.; Abe, a.; Fukasawa, T. *Molecular and Cell Biology* 8, 4991–4999 (1988), Long, R. M.; Mylin, L. M.; Hopper, J. E. *Molecular and Cell Biology* 11, 2311–2314 (1991). It is suspected that proteins containing the Gal 4 region that recognizes Gal 11p in vivo interact in vitro with Gal 11p but not with Gal 11 (wild type).

It is also suspected that Gal 4 promotes transcription by facilitating the necessary proximity of a holoenzyme containing Gal 11 with the TATA box on DNA. It has been reported that Gal 4, truncated to completely abolish its activating domain, is transcriptionally active in the presence of the holoenzyme containing Gal 11p (but not in the presence of the holoenzyme containing Gal 11). Accordingly, it has been postulated that Gal 11p interacts hydrophobically with truncated Gal 4 to facilitate transcription.

SPR was used to study the interaction of Gal 4 with the immobilized his-tagged Gal 11p. It was observed that Gal 11p binds Gal 4, but does not bind a number of other transcription promoters. Histidine-tagged wild-type Gal 11, immobilized on the SPR chip in the same manner, did not bind Gal 4. None of the transcription promoters demonstrate NSB on the mixed monolayer. That is, in the absence of Gal 11p immobilized on the surface, no transcription promoters bound to the surface, and in the presence of immobilized Gal 11p, only Gal 4 was bound.

The interaction between Gal 11p and Gal 4 was not observed by co-immunoprecipitation or on an affinity column, demonstrating the importance of the orientation in the presentation of the protein to the analyte solution, achievable in accordance with the present invention.

Example 6: Comparative Attempted SPR Determination of SRB2 Using Standard Dextran Chip Carrying Gal 11

This example examines the sensitivity of the current state-of-the-art SPR chip, which comprises a layer of dextran on the gold SPR chip surface.

In this example, an attempt was made to study the interaction of Gal 11 (wild-type) and the RNA polymerase B suppressor SRB2, a 28 kD member of the holoenzyme described in example 5 (the multi protein complex which assembles on the DNA at the TATA box and with which a DNA-bound activator must interact in order to activate transcription). Koleske, a. J.; Young, R. A. *Nature*, 368, 466–469 (1994). As discussed in example 5, Gal 11p interacts with Gal 4, thus it is important to find a target of Gal 11 on the holoenzyme. Detection of this type of interaction is difficult because transcription factors generally exhibit low affinity for their targets, such that positive control of transcription of achieved only through the correct assembly of several factors. The 30 kD protein SRB5 was used as a negative control in this example. SRB5 is shown by genetic experiments not to interact with Gal 11 or Gal 11p Id.

An SPR chip having a layer of dextran on gold (#BR1000-14) was purchased from Pharmacia Biosensor., and the SPR instrument described above was employed.

FIG. 1 illustrates a sensorgram plotting resonance units (RU) as a function of time associated with this example. The flow rate of sample across the chip surface was 5 ul/min. The sensorgram of FIG. 1 is labeled with reference numerals that correspond to the steps of the experimental protocol below.

1. (t=240 sec) description of chip type; standard dextran
2. (t=731 sec) end of injection of EDC/NHS which activates the carboxylates on the dextran surface.
3. (t=13 26 sec) end of injection of 35 ul wild type Gal 11 at 0.025 mg/ml, in NaOAc buffer at pH 4.5.
4. (t=1440 sec) preinjection baseline
5. (t=1928 sec) end of injection of ethanolamine, which blocks the activated carboxylates that did not covalently link to a protein.
6. (t=2179 sec) preinjection baseline
7. (t=2668 see) end of injection of SRB2 at 0.25 mg/ml diluted with the running buffer PBS.
8. (t=2991 sec) preinjection baseline
9. (t=3472 sec) end of injection of SRB2 at 0.5 mg/ml
10. (t=3639 sec) preinjection baseline
11. (t=4122 sec) end of injection of SRB5 at 0.25 mg/ml
12. (t=4218 sec) preinjection baseline
13. (t=4814 sec) end of injection of SRB5 at 0.5 mg/ml
14. (t=5610 sec) preinjection baseline
15. (t=6128 sec) end of injection of myc-a, a monoclonal antibody which should bind to Gal 11, at 0.25 mg/ml.

Tabulated below are protein absorption response values (AbsResp; RU units) and response values relative to preceding baseline (RelResp; RU units) corresponding to the protocol steps above.

|  | Time | AbsResp | RelResp |
|---|---|---|---|
| 1. | 240.00 | 9150 |  |
| 2. | 731.00 | 9313 |  |
| 3. | 1326.50 | 13444 | 4131 |
| 4. | 1440.00 | 13291 | 3978 |
| 5. | 1928.00 | 12950 | 3637 |
| 6. | 2179.00 | 12872 | 3559 |
| 7. | 2668.00 | 12923 | 51 |
| 8. | 2991.00 | 12880 | 8 |
| 9. | 3472.00 | 12976 | 96 |
| 10. | 3639.00 | 12895 | 15 |
| 11. | 4122.00 | 12911 | 17 |
| 12. | 4218.00 | 12887 | −8 |
| 13. | 4814.00 | 12941 | 54 |
| 14. | 5610.00 | 12852 | −35 |
| 15. | 6128.00 | 12940 | 87 |

4131 RUs of Gal 11 bound to the dextran. The interaction of Gal 11 with SRB2 yielded an absorption of 51 RU's at [SRB2]=0.25 mg/ml; at [SRB2]=0.50 mg/ml, the absorption was 96 RUs. By contrast, at [SRB5]=0.25 mg/ml the absorption was 17 RUs, while at [SRB5]=0.5 mg/ml, the absorption was 54 RUs. Lastly, at [myc-a]=0.25 mg/ml, the absorption was 87 RU's.

Since the negative and positive controls (SRB5 and myc-a, respectfully) gave essentially the same results, no conclusions regarding binding can be reached. This example demonstrates that the current state-of-the-art dextran chip does not provides the sensitivity necessary for determination of biological binding between Gal 11 and SRB2.

Example 7: SPR Determination of SRB2 Using Chip Derivatized With Self-Assembled Monolayer of Alkyl Thiol Terminating In Metal Chelate Coordinated By Polyamino Acid-Tagged Gal 11

As in example 5, this example demonstrates the sensitivity of the SPR technique using a chip derivatized in accordance with the present invention. An SPR chip prepared in accordance with example 2 was mounted in the instrument, modification of the chip to chelate nickel dication was effected in accordance with example 3, the modified chip surface was exposed to histidine-tagged Gal 11, and SPR response to introduction to the chip surface of SRB2 and SRB5 was investigated.

FIG. 2 illustrates a sensorgram plotting resonance units as a function of time associated with this example. The flow rate of sample across the chip surface was 5 ul/min. The sensorgram of FIG. 2 is labeled with reference numerals that correspond to the steps of the experimental protocol below.

1. (t=50 s) chip description; 5 Ni ligand
2. (t=390 s) end of injection of 1 mM NaOH 3. (t=993 s) end of injection of 1% $NiSO_4$
4. (t=1055 s) preinjection baseline
5. (t=1555 s) end of injection of Gal 11 at 0.025 mg/ml
6. (t=1703 s) preinjection baseline
7. (t=2222 s) end of injection of a second Gal 11 injection at the same concentration to achieve maximum chip coverage.
8. (t=2343 s) preinjection baseline
9. (t=2821 s) end of injection of SRB2 at 0.25 mg/ml
10. (t=2932 s) preinjection baseline
11. (t=-3438 s) end of injection of SRB2 at 0.5 mg/ml
12. (t=3610 s) preinjection baseline
13. (t=4116 s) end of injection of SRB5 at 0.25 mg/ml
14. (t=4238 s) preinjection baseline
15. (t=4728 s) end of injection of SRB5 at 0.5 mg/ml
16. (t=4842 s) preinjection baseline
17. (t=5330 s) end of injection of myc-a at 0.25 mg/ml Tabulated below are protein absorption response values (AbsResp; RU units) and response values relative to preceding baseline (RelResp; RU units) corresponding to the protocol steps above.

|  | Time | AbsResp | RelResp |
|---|---|---|---|
| 1. | 50.50 | 8297 |  |
| 2. | 390.00 | 8258 |  |
| 3. | 993.00 | 8374 |  |
| 4. | 1055.00 | 8368 | 0 |
| 5. | 1555.50 | 9122 | 753 |
| 6. | 1703.00 | 8887 | 519 |
| 7. | 2222.00 | 9197 | 828 |
| 8. | 2343.00 | 9042 | 673 |
| 9. | 2821.00 | 10998 | 1956 |
| 10. | 2932.00 | 10927 | 1885 |
| 11. | 3438.00 | 11174 | 2132 |
| 12. | 3610.00 | 11090 | 2048 |
| 13. | 4116.00 | 11138 | 47 |
| 14. | 4238.00 | 11100 | 10 |
| 15. | 4728.00 | 11174 | 73 |
| 16. | 4842.00 | 11129 | 28 |
| 17. | 5330.00 | 11578 | 450 |

In contrast to the prior art embodiment examined in example 6, substantial binding of SRB2 to immobilized Gal 11 was observed. Importantly, no nonspecific binding of SRB5 to Gal 11 was observed. Specifically, 673 RUs of histidine-tagged Gal 11 bound to the surface exposing chelate coordinating nickel dication. The interaction of Gal 11 with SRB2 yielded an absorption of 1956 RUs at [SRB2]=0.25 mg/ml; at [SRB2]=0.50 mg/ml, the absorption increased by an additional 176 RU's for a total of 2132 RU's of bound protein. By contrast, at [SRB5]=0.25 mg/ml the absorption was 47 RUs, while at [SRB5]=0.5 mg/ml, the absorption was 73 RUs. Lastly, at [myc-a]=0.25 mg/ml, the absorption was 450 RU's. These results clearly show that the biological molecule SRB2 bound to its binding partner Gal 11. The negative control SRB5 did not bind, and the positive control myc-a did bind.

As additional control experiments: (1) SRB2 was brought into contact with a chip incorporating a metal ion (prepared in accordance with example 3) that did not have coordinated to it a the binding partner Gal 11, and (2) SRB5 was flowed over the chip after coordination of Gal 11 prior to the introduction of SRB2. No significant binding was observed in either case.

This experiment demonstrates that a biosensor surface prepared in accordance with the present invention, which provides biological binding partners oriented to stably expose recognition regions to an analyte solution, is superior to the prior art surface.

Example 8: Comparative Attempted SPR Determination of Monoclonal Antibodies Using Standard Dextran Chip Carrying T Cell Receptor As in example 5, this example examines the sensitivity of the current state-of-the-art SPR chip, which comprises a layer of dextran on the gold SPR chip surface.

In this example, an attempt was made to study the interaction of a soluble 42 kD chimeric T cell receptor (TCR), herein referred to as ABC, with 2 monoclonal antibodies of MW 155 kD (C1 and βF1). C1 recognizes a conformational epitope thought to be near the active site of the receptor, while βF1 recognizes a linear epitope of the constant domain. Although the structure of a TCR has not yet been solved, by analogy to IG structure, the C1 epitope should reside near the "top" of the protein and the βF1 epitope near the "bottom", where the bottom is defined as the histidine tag of the protein. Probing the TCR with C1 demonstrated the availability of a defined site on the protein. The ratio of C1:βF1 binding is the ratio of correctly:incorrectly folded protein, since C1 was shown to occlude the binding site of βF1 when the TCR is bound to a surface (data not shown).

FIG. 3 illustrates a sensorgram plotting resonance units as a function of time associated with this example. The flow rate of sample across the chip surface was 5 ul/min. The sensorgram of FIG. 3 is labeled with reference numerals that correspond to the steps of the experimental protocol below.

1. (t=470 s) end of injection of EDC/NHS
2. (t=1044 s) end of injection of ABC at 0.125 mg/ml in PBS buffer
3. (t=1579 s) end of injection of ethanolamine
4. (t=2047 s) end of injection of C1 at 0.2 mg/ml in PBS
5. (t=2630 s) end of injection of SF1 at 0.2 mg/ml in PBS
6. (t=3152 s) end of injection of myc-a. at 0.2 mg/ml in PBS Tabulated below are protein absorption response values (AbsResp; RU units) and response values relative to preceding baseline (RelResp; RU units) corresponding to the protocol steps above.

|  | Time | AbsResp | RelResp |
|---|---|---|---|
| 1. | 470.50 | 8717 |  |
| 2. | 1044.00 | 25276 | 16558 |
| 3. | 1579.00 | 22216 | 13499 |
| 4. | 2047.00 | 22675 | 459 |
| 5. | 2630.00 | 23728 | 1512 |
| 6. | 3152.00 | 23658 | 1442 |

13,499 RU's of ABC bound to the dextran surface. The interaction with C1 led to an absorption increase of 459 RUs, while that with βF1 led to an additional 1053 RU's. Finally, the myc-a antibody did not bind. The ratio of C1:ABC was 1:29. The ratio of C1:B1 was 1:2.3. Since the molecular weight of C1 is 3.7 times that of ABC, the molar ratio of C1:ABC is 1:108, which implies that only 0.9% of the ABC molecules were recognized by C1.

This experiment demonstrates that the current state-of-the-art dextran chip does not provide the sensitivity necessary for determination of biological binding between ABC and C1.

Example 9: SPR Determination of Monoclonal Antibodies Using Chip Derivatized With Self-Assembled Monolayer of Alkyl Thiol Terminating In Metal Chelate Coordinated By Polyamino Acid-Tagged T Cell Receptor As in examples 5 and 7, this example demonstrates the sensitivity of the SPR technique using a chip derivatized in accordance with the present invention. An SPR chip prepared in accordance with example 2 was mounted in the SPR instrument described above, modification of the chip to chelate nickel dication was effected in accordance with example 3, the modified chip surface was exposed to ABC (example 8) including a histidine tag at the constant domain, and SPR response to introduction to the chip surface of C1 and F1 was investigated.

FIG. 4 illustrates a sensorgram plotting resonance units as a function of time associated with this example. The flow rate of sample across the chip surface was 5 ul/min. The sensorgram of FIG. 4 is labeled with reference numerals that correspond to the steps of the experimental protocol below.

1. (t=42 s) chip description
2. (t=448 s) end of injection of 1 mM NAOH
3. (t=1017 s) end of injection of 1% $NiSO_4$
4. (t=1097 s) preinjection baseline
5. (t=1553 s) end of injection of ABC at 0.125 mg/ml; solution contains 0.02M imidazole
6. (t=1696 s) preinjection baseline
7. (t=2177 s) end of injection of C1 at 0.2 mg/ml; solution contains 0.02M imidazole
8. (t=2288 s) preinjection baseline
9. (t=2781 s) end of injection of SF1 at 0.2 mg/ml; solution contains 0.02M imidazole
10. (t=3075 s) preinjection baseline
11. (t=3604 s) end of injection of myc-a at 0.2 mg/ml; solution contains 0.02M imidazole Tabulated below are protein absorption response values (AbsResp; RU units) and response values relative to preceding baseline (RelResp; RU units) corresponding to the protocol steps above.

|     | Time    | AbsResp | RelResp |
| --- | ------- | ------- | ------- |
| 1.  | 42.00   | 7671    |         |
| 2.  | 448.50  | 7660    |         |
| 3.  | 1017.50 | 7730    |         |
| 4.  | 1097.00 | 7695    |         |
| 5.  | 1553.50 | 9640    | 1945    |
| 6.  | 1696.00 | 9634    | 1939    |
| 7.  | 2177.00 | 10376   | 742     |
| 8.  | 2288.00 | 10353   | 719     |
| 9.  | 2781.00 | 10761   | 408     |
| 10. | 3075.00 | 10739   | 386     |
| 11. | 3604.00 | 10830   | 91      |

1,945 RU's of ABC bound to the Ni surface. The interaction with C1 led to an absorption increase of 719 RU's, while that with βF1 led to an additional 386 RU's. Finally, the myc-a antibody binding led to a 91 RU increase. The ratio of C1:ABC was 1:2.7. The ratio of C1:βF1 was 1.9:1. Since the molecular weight of C1 is 3.7 times that of ABC, the molar ratio of C1:ABC is 1:10, which implies that 10% of the ABC molecules were recognized by C1. In separate in vivo inhibition assays, we consistently found that 10% of the ABC was correctly folded, We therefore conclude that in this example 100% of the correctly folded ABC was oriented on the gold chip with the C1 binding site in the accessible "up" position with respect to the chip surface. This is in contrast to 9% retained activity in example 8.

This example demonstrates that essentially all of the binding partners immobilized at the chip surface in accordance with the present invention were oriented so as to expose in a direction away from the chip surface the recognition region of the binding partner for the biological molecule sought to be captured.

Example 10: Fabrication of Chip Derivatized with Self-Assembled Monolayer of Alkyl Thiol Terminating In Biological Binding Partner of DNA, To Expose DNA For Binding Studies This prophetic example describes preparation of an alkyl thiol terminating at its exposed end in a nucleic acid sequence, and a surface derivatized to carry a self-assembled monolayer including such species. Specifically, an SPR chip is primed to receive underderivatized dsDNA, provided by the user, which has been modified by the generation of an EcoR I site at one end.

a protected, single-stranded oligo is prepared via standard methods, as described in the Gene Assembler manual, Pharmacia Biosensor. The oligo is at least 25 base pairs long, and is a mixed, nonself-complementary sequence, terminated with a dG at the 3' end. The polymer-supported oligo is dried under vacuum overnight.

The 5' dimethoxytrityl (DMT) protecting group is deprotected at pH 3.0 in water for 10 minutes at room temperature. The reaction is stopped by freezing on dry ice, and the residue is filtered. See Ferentz, a.; Keating, T. a.; Verdine, G. L. *J. Am. Chem. Soc.* 115, 9006–9014 (1993)

From 11-mercaptoundec-1yl oligo(ethyleneglycol) (6; see example 2) is synthesized the S-DMT-protected derivative. See Zervas, L. L.; Photaki, I. *J Am. Chem. Soc.* 84, 3887–3891 (1962). The 5' hydroxyl of the oligo is activated with carbonyl diimidazole. See Wachter, I.; Jabloski, J. a.; Ramachandran, K. L. *Nucleic Acids. Res.* 14, 7985–7994 (1986).

The protected alkyl thiol is added to the activated oligo in dioxane water for 30 minutes at room temperature. Excess reagent is washed away with dry dioxane, followed by methanol, and the product is dried in a desiccator overnight. The remaining protecting groups and the solid support are deprotected by treating with 25% aqueous ammonia for 6 hours at 60° C. The aqueous ammonia is chilled at 0° for 30 minutes, the polymer support is filtered, and the ammonia evaporated.

The derivatized oligo is purified via 8% PAGE-7M urea, then via G-10 Sephadex chromatography. The oligo is reduced with silver nitrate/DTT and rechromatographed. See Connolly, B. a.; Rider, P. *Nucleic Acids Res.* 12, 4485–4502 (1985).

An oligo of sequence complementary to that made in step 1, with an additional 4 bp's at the 5' end (3'-TTAA-5') is purchased. The purified, derivatized oligo from the previous step is hybridized with the complementary oligo by denaturation at 75° C., and annealed at 55° C. This yields an alkyl thiol attached to a dsDNA, which is terminated with an EcoR I restriction enzyme site. EcoR I is widely available commercially, for example from New England Biolabs.

This DNA ligand is mixed with a self-assembled monolayer-forming, nonspecific binding-inhibiting species, specifically, 11-mercaptoundec-1yl oligo(ethyleneglycol) (6; see example 2) in a 5:95 molar ratio, respectively. The chip surface is prepared as described in example 2. This completes the preparation of a commercial chip.

Example 11: Modification of Chip Derivatized With Self-Assembled Monolayer of Alkyl Thiol Terminating In Biological Binding Partner of DNA, To Expose DNA For Binding Studies In this prophetic example, selected dsDNA that the user wishes to present on the chip surface is cut, via standard methods, with EcoR I. The cut DNA is ligated to the DNA already on the chip using DNA ligase (New England Biolabs). The chip is now ready for use in a biosensor.

Advantages of the chip prepared in accordance with examples 10 and 11 follow. The current state-of-the-art chip, available from Pharmacia Biosensor for use in the BIAcore™ SPR instrument, presents a dextran surface to which strepavidin is attached. The user must either derivative the desired DNA with biotin, or purchase biotinylated DNA. In the former case, the reaction is difficult and biotinylation may occur at any number of sites, leading to a lack of control over orientation on the chip. Furthermore, biotinylation may block an interaction site on the DNA. Commercially available biotinylated DNA is very expensive and cannot be obtained in lengths much greater than 70 base pairs. The derivatized DNA then is attached to the chip surface via interaction between the biotin and the strepavidin.

Another disadvantage of the prior art strepavidin/biotin technique includes the fact that many of the compounds which bind negatively charged DNA are positively charged. Since the dextran surface retains a number of negatively charged carboxylates, interactions of an electrostatic nature may be mistaken for binding with the target DNA. Also, kinetic analyses of binding would be compromised due to the additional attractive force created by the negative carboxylates. Still another disadvantage of the prior art technique is that the strepavidin on the chip surface gives rise to nonspecific interactions with many target compounds.

The procedure described in this example for the preparation of the DNA chip may be applied to the preparation of an analogous RNA chip.

Example 12: Fabrication and Modification of Chip Derivatized With Self-Assembled Monolayer of Alkyl Thiol Terminating In Biological Binding Partner of DNA, To Expose DNA For Binding Studies This example describes preparation of a SAM terminating at its exposed end in a nucleic acid sequence, and a surface derivatized to carry a self-assembled monolayer including this species in combination with a background layer of inert SAM-forming species. In particular, a SAM presenting short strands of single-stranded DNA (ssDNA; 34, with reference to FIGS. 8–10) above a background layer of inert non-binding thiols 30 was prepared, followed by hybridization of double-stranded DNA containing specific protein binding sites to the chip surface, the double-stranded DNA having a single stranded tail complementary to that presented by the chip. Specifically, an SPR chip was primed to receive underderivatized dsDNA modified by the generation of an EcoR I site at one end.

An SAM-forming nucleic acid species 34 was synthesized as follows. Species (1) was reacted with tosyl chloride in pyridine at room temperature for 4–6 hours to give species (8):

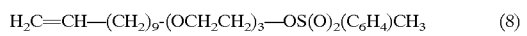

This was reacted with $NaN_3$ in N,N-dimethylformamide at 60° C. for approximately 4–8 hours giving species (9):

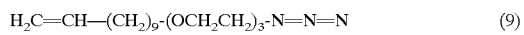

Species (9) was reacted according to one of two methods. In the first method, species (9) was reacted with $PPh_3$ in THF followed by reaction with water. In a preferred method, reaction took place with $LiAlH_4$, refluxing for two hours in THF, followed by reaction with water. In either case species (10) was recovered:

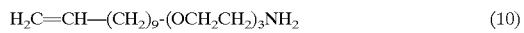

Species (10) was reacted with $(CH_3)_3C-O-C(O)-O-C(O)-O-C(CH_3)_3$ and $Et_3N$ in DMF for 0.5 hours at 50° C. giving species (11):

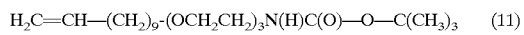

which was reacted with six equivalents of $CH_3C(O)SH$ and $CH_3-C(CH_3)$ (CN)—N=N—$C(CH_3)$ (CN)—$CH_3$. The reaction mixture was irradiated with a medium pressure 450 Watt lamp (Hanovia) for five hours giving species (12):

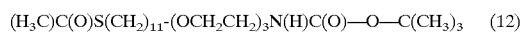

Species (12) was reacted with Hcl/MeOH(0.1M) and refluxed for 4–6 hours to give species (13):

which was reacted with $I_2$, $O_2$, and $CH_3(CH_2)_3SH$ in dimethoxyethane for 4 hours to give species (14):

A 10-base strand of DNA was synthesized on a DNA synthesizer. While still attached to the resin, the 5'-deprotected DNA was reacted with carbonyldiimidazole (CDI) to give the 5'-imidazolylacylated product. This was subsequently reacted with species (14), first in dioxane for 0.5–1 hour, then with $NH_3$ at 60° C. for 6–8 hours to give species (15):

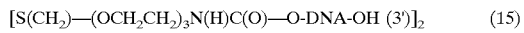

Species (15) was removed from the resin by standard purification techniques except that $NH_4OH$ at 65° C for 8 hrs was used, giving (16):

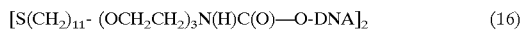

The product, after removal from resin after purification (HPLC), was a thiol derivatized with single-stranded DNA. HPLC analysis showed the generation of a new species (50–75% pure) that eluted from the column upon purification much later than the underivatized 10-mer DNA and slightly slower than the 10-mer DNA with the trityl group still attached to the 5' end. The elution profile of the product is consistent with expected results for DNA derivatized with the alkyl thiol chain.

Species (16) formed pairs of exposed nucleic acid strands, with the —S—S-bridge in the center of the molecule adhering to the surface. Species (16) is represented as species 34 in the figures.

The selected dsDNA desirably immobilized at the surface was then cut, via standard methods, with EcoR I. The cut DNA was ligated to the DNA already on the chip using DNA ligase, resulting in a chip ready for use in a biosensor.

To form a self-assembled monolayer, SAM-forming ssDNA species (16; 34 in the figures) was mixed with the inert, non-binding ethyleneglycol-terminated thiol (6; 30 in the figures) in mM ethanol solution in a molar percent of inert species of about 0.5–3%. A gold 26-coated glass substrate 22 then was incubated in this solution. A SAM 28 was formed on the gold surface 24. It was assumed that any DNA not derivatized with thiol did not bind the gold surface. Additionally, any amino-thiol that did not react with the 5' hydroxyl of the DNA would have been lost during the extensive washing steps while the DNA was still resin-bound. Therefore, DNA-SAMs were formed without further purification. Good SAM formation from acetonitrile was significantly more effective than from ethanol, forming (per SPR analysis) ordered SAM arrays when the gold substrate was incubated at 45° C. for 12 hours. The surfaces were well behaved in that they resisted the binding of proteins and (as FIGS. 5–7 and related discussion show) these surfaces hybridized DNA if and only if the DNA had a single stranded tail of exactly complementary sequence to that presented by the chip.

Once dsDNA 36 was hybridized to the covalently-immobilized single-stranded DNA 34 at the surface, the nick 40 in the coding strand was covalently joined by DNA ligase but only in cases in which the 5' hydroxyl of the incoming oligo was phosphorylated. It was observed that performing a DNA ligation reaction resulted in more DNA stably bound to the surface but only if the 5' hydroxyl was first phosphorylated. When DNA containing Gal4 recognition sites was hybridized to the DNA-SAM, it selectively bound Gal4 protein but not another DNA-binding protein Lex-B17. Our results indicate that we have generated a DNA-presenting SAM.

Example 13: Characterization of Chip Derivatized With Self-Assembled Monolayer of Alkyl Thiol Terminating In Biological Binding Partner of DNA Varying amounts of the ssDNA-derivatized disulfide (16) were mixed with the inert, tri-ethylene glycol terminated thiol (6) which defined the major component (1 mM) in acetonitrile solutions. Pre-cleaned ($H_2SO_4/H_2O$), gold-coated glass slides were incubated at 45° C. for 8–12 h in the solutions. The slides were cut and mounted on plastic CM-5 SPR chip cassettes (Pharmacia). The experimental chips were docked in a BIACore™ SPR instrument and experiments were performed to assay the ability of the chip to hybridize single-stranded DNA (ssDNA) complementary to the strand of the DNA-derivatized thiol.

Three DNA samples were sequentially injected over the same flow cell of a chip. The samples contained double-stranded DNA (dsDNA) containing 2 Gal4 protein binding sites and the three DNA samples included: 1) DNA without a single-stranded tail, 2) DNA with a 10-base single stranded tail whose sequence content was complementary to strand 34 presented by the chip, but having a scrambled sequence and 3) DNA with a 10-base single stranded tail exactly complementary to that presented by the chip. 35 μL of each DNA sample (DNA concentration=[14 pM/μL] in 400 mM NaCl) as separately injected over the DNA-SAM. Experiments were run at RT at a constant flow rate of 5 μL/min in PBS (137 mM NaCl). As discussed above, the binding of molecules to a chip surface is detected as a net increase in resonance units (RUs). A net change in RUs resulted only after the injection of sample (3), that is, the DNA bearing a single-stranded tail whose sequence was exactly complementary to strand 34 of the DNA-thiol SAM immobilized on the chip.

FIG. 5 illustrates a sensorgram plotting RU as a function of time associated with the experiments involving DNA with a single-stranded scrambled tail and DNA with a 10-base single stranded tail complementary to nucleic acid strand 34 presented by the chip. The sensorgram of FIG. 5 is labeled with reference numerals that correspond to the steps of the experimental protocol below.

1. (t=130 sec) end of injection of 137 mM NaCl buffer.
2. (t=205 sec) preinjection baseline.
3. (t=519 sec) end of injection of DNA with 10-base single-stranded scrambled "tail".
4. (t=624 sec) preinjection baseline.
5. (t=1003 sec) end of injection of DNA with 10-base single-stranded tail complementary to that presented by the chip.

Tabulated below are DNA absorption response values (AbsResp; RU units) and response values relative to preceding baseline (RelResp; RU units) corresponding to the protocol steps above.

|    | Time    | AbsResp | RelResp |
|----|---------|---------|---------|
| 1. | 130.50  | 11726   | −4      |
| 2. | 206.50  | 11722   | −7      |
| 3. | 519.50  | 11719   | −3      |
| 4. | 624.50  | 11710   | −8      |
| 5. | 1003.00 | 11822   | 112     |

FIG. 6 is a sensorgram plotting RU as a function of time associated with injection of DNA without a single-stranded tail. The sensorgram of FIG. 6 is labeled with reference numerals that correspond to the steps of the experimental protocol below.

1. (t=259 sec) chip description
2. (t=787 sec) end of injection of DNA without tail Tabulated below are DNA absorption response values and response values relative to preceding baseline corresponding to the protocol steps above.

|    | Time   | AbsResp | RelResp |
|----|--------|---------|---------|
| 1. | 259.00 | 12380   | 0       |
| 2. | 787.00 | 12383   | 2       |

This experiment demonstrates that a biosensor surface prepared in accordance with the invention provides a nucleotide sequence oriented to expose away from the chip surface the nucleotide 34 for binding to a complementary nucleotide.

We found that the DNA hybridized to the chip was more stably bound if it was enzymatically ligated to the DNA presented by the chip. To do this, the chips were docked in the BIAcore™ SPR instrument and equilibrated in PBS. Baseline measurements were recorded for each flow cell. The chips were then removed from the instrument and were bathed in 100 μL of a solution containing DNA with a 10-base single-stranded tail complementary to strand 34 presented by the chip for 0.5 h at RT. The excess solution was removed from the chip surface and 200 μL of DNA ligase in ligase buffer was added to mend nick 40 in the strand. The stability of the bound DNA increased if and only if DNA ligase was present and the 5' end of the incoming synthetic DNA strand was phosphorylated. These results reflect the advantage of using DNA ligase to join two DNA strands through a 5' phosphate group.

Example 14: SPR Determination of Specific Protein Binding to DNA Chip

Experiments were performed to determine whether these chips as described in Example 13 could specifically bind proteins to binding sites on the hybridized DNA while resisting the non-specific adsorption of irrelevant proteins. In particular, SPR experiments were conducted to investigate the binding of Gal4(1–100) as opposed to Lex-B17 on chips carrying hybridized DNA bearing 2Gal4 protein binding sites. FIG. 7 is a sensorgram plotting resonance unit as a function of time associated with this example. The sensorgram of FIG. 7 is labled with reference numerals that correspond to the steps of the experimental protocol below.

1. (t=77 sec) chip description
2. (t=335 sec) end of injection of 137 mM NaCl
3. (t=677 sec) end of injection of DNA including 10-base pair complementary to that presented by the chip
4. (t=923 sec) preinjection baseline
5. (t=1275 sec) end of injection of Lex-B17 (0.125 mg/ml)
6. (t=1327 sec) preinjection baseline
7. (t=1700 sec) end of injection of Gal4 (0.125 mg/ml)

Tabulated below are protein absorption response values and response values relative to preceding baseline corresponding to the protocol steps above.

|    | Time    | AbsResp | RelResp |
|----|---------|---------|---------|
| 1. | 77.50   | 10651   | 0       |
| 2. | 335.50  | 10658   | 7       |
| 3. | 677.50  | 10791   | 133     |
| 4. | 923.00  | 10732   | −59     |
| 5. | 1275.50 | 10762   | 29      |
| 6. | 1327.50 | 10741   | −20     |
| 7. | 1700.00 | 10955   | 213     |

Experiments were performed also to determine whether the concentration of the SAM-forming nucleotide on the chip had an effect on protein binding. Table 1 shows a comparison of four different chips with different DNA concentration at the chip surface, the DNA including 2 Gal4 protein binding sites.

TABLE 1

| dsDNA CONTAINING 2 GAL4 BINDING SITES (Δ RUs) | GAL4 BOUND (RUs) | LEX B17 BOUND (RUs) |
|---|---|---|
| 52   | 164  | —  |
| 74   | 213  | 0  |
| 441  | 365  | —  |
| 1378 | 1079 | 96 |

SPR experiments showed that hybridized DNA bearing 2 Gal4 protein binding sites preferrentially bound Gal4 (1–100) protein over Lex-B17. Additionally, there appears to be a direct correlation between the amount of DNA hybridized to the chip and the amount of Gal4 that subsequently bound to it.

The observed preference of chip-hybridized DNA containing Gal4 binding sites for Gal4 protein over Lex-B17 was reversed when DNA bearing Lex binding sites was hybridized to the chip surface (see Table 2). DNA containing 2 Lex binding sites and a single-stranded complementary tail was annealed, then ligated to a ssDNA chip. The chip was then docked in a BIAcore™ SPR instrument and equimolar concentrations of either Lex-B17 or Gal4 were separately passed over three flow cells of the same chip.

TABLE 2

| FLOW CELL | GAL4 BOUND (RUs) | LEX B17 BOUND (RUs) |
|---|---|---|
| 1 | —   | 363 |
| 2 | 136 | —   |
| 3 | —   | 345 |

Example 15: Reversible Hybridization of Double-Stranded DNA Specific for LEX-B17 and Confirmation of Specificity In this example, hybridization, disassociation, and re-hybridization of dsDNA specific for LEX-B17 is demonstrated, along with the specificity of the dsDNA for the protein.

A chip was prepared as described in Example 13 and illustrated in FIG. 8 including an SAM having, as a minor component, a nucleotide 34. dsDNA 36 was hybridized to strand 34, the nick in the coating strand was ligated, and restriction enzyme 46 used to cut the dsDNA on the chip.

As illustrated in FIG. 10, dsDNA having a binding site for LEX-B17, and having been cut with restriction enzyme 46, was hybridized to DNA 48 presented by the chip, but the nick in the coating strand was not mended. Hot water was injected to remove strand 56, and strand 56 was allowed to re-hybridized to strand 54, and the process was shown to be repeatable. Following repetition of disassociation and re-hybridization of strand 56 to strand 54, immobilized dsDNA 52 was shown to be specific for Lex-B17, while NSB of Gal 4 was very low. After confirmation of specificity for Lex-B17, strand 56 could be disassociated and re-hybridized and the specificity for Lex-B17 demonstrated again.

This example demonstrates the robustness of single-stranded DNA, immobilized at a surface, even when not covalently linked to the surface.

Those skilled in the art would readily appreciate that all parameters listed herein are meant to be exemplary and actual parameters will depend upon the specific application for which the methods and apparatus of the present invention are being used. It is, therefore, to be understood that the foregoing embodiments are presented by way of example only and that, within the scope of the appended claims and equivalents thereto, the invention may be practiced otherwise than as specifically described.

What is claimed is:

1. A composition comprising a self-assembled monolayer-forming species wherein at least one of said self-assembled monolayer forming species has a formula X—R—NA—NAB, wherein NA represents a nucleic acid strand and NAB represents a biological binding partner of NA.

2. A composition according to claim 1 wherein NAB is a nucleic acid strand that is a binding partner of NA.

3. A composition comprising:
   a) a surface; and,
   b) a first species having a formula X—R—NA—NAB, wherein X represents a functional group that adheres to said surface, R represents a spacer moiety that promotes formation of a self-assembled monolayer of a plurality of said species, NA represents a nucleic acid strand, and NAB represents a biological binding partner of NA.

4. A composition according to claim 3 further comprising a second species that will form a mixed self-assembled monolayer with said first species.

5. A composition according to claim 4 wherein said second species has the formula X—R.

6. A composition according to claim 4 wherein said second species has the formula X—R—O—(—CH$_2$-CH$_2$-O)$_n$-H, wherein n is from 1 to 10.

7. A composition according to claim 3 wherein X is a sulfur containing functional group.

8. A composition according to claim 3 wherein R is a hydrocarbon chain optionally interrupted by at least one hetero group.

9. A composition according to claim 5 or 8 wherein R has the formula —(CH$_2$)$_n$-, wherein n is from about 8 to about 24.

10. A composition according to claim 3 wherein said surface comprises gold.

11. A composition according to claim 4 wherein said second species has a formula X—R—NSBi, wherein NSBi is a non-specific binding inhibitor.

12. A composition according to claim 3 wherein NAB is a nucleic acid strand that is a binding partner of NA.

13. A composition according to claim 3 wherein NA comrises a single stranded nucleic acid strand.

14. A composition according to claim 3 wherein NAB comprises a single stranded nucleic acid strand.

* * * * *

UNITED STATES PATENT AND TRADEMARK OFFICE
CERTIFICATE OF CORRECTION

PATENT NO. : 6,472,148 B1
DATED : October 29, 2002
INVENTOR(S) : Cynthia C. Bamdad et al.

It is certified that error appears in the above-identified patent and that said Letters Patent is hereby corrected as shown below:

Title page,
Item [56], References Cited, FOREIGN PATENT DOCUMENTS,
change "EP 0 589 867 5/1990" to -- EP 0 589 867 4/1996 --
change "JP 6-41183 3/1994" to -- JP 6-41183 2/1994 --
OTHER PUBLICATIONS, reference to "Hsung et al.," change "(X -SH, sMe," to
-- (X =SH, Sme, --
Item [74], *Attorney, Agent, or Firm*, change "Altritton & Herbert LLP" to
-- Flehr Hohbach Test Albritton & Herbert LLP --

Column 2,
Line 39, change "can not" to -- cannot --

Column 3,
Line 39, change "car" to -- can --

Column 12,
Line 3, change "preferably 1-3)," to -- preferably 1-8), --
Line 32, change "$Al^{+3}$," to -- $Al^{3+}$, --

Column 15,
Line 34, change "resrictive" to -- restrictive --

Column 16,
Line 38, change "it: is" to -- it is --

Column 19,
Line 49, change "$H_2SO_4/H_2O$" to -- $H_2SO_4/H_2O_2$ --

Column 20,
Line 9, change "$CH(CO_2H)(N(CH_2CO_2H)2.Ni^{2+}$" to
-- $CH(CO_2H)(N(CH_2CO_2H)_2.Ni^{2+}$ --
Line 15, change "(potentiator)" to -- (potentiator) --
Lines 19 and 24, change "lip" to -- 11p --

Column 21,
Line 66, change "see" to -- sec --

Column 22,
Line 66, change "5 Ni" to -- 5% Ni --

UNITED STATES PATENT AND TRADEMARK OFFICE
CERTIFICATE OF CORRECTION

PATENT NO.    : 6,472,148 B1
DATED         : October 29, 2002
INVENTOR(S)   : Cynthia C. Bamdad et al.

It is certified that error appears in the above-identified patent and that said Letters Patent is hereby corrected as shown below:

Column 23,
Line 11, change "11. (t-3438 s)" to -- 11. (t=3438 s) --

Column 24,
Line 14, change "MW 155" to -- MW-155 --

Column 24,
Line 38, change "SF1" to -- βF1 --

Column 25,
Line 15, change "F1" to -- βF1 --
Line 33, change "SF1" to -- βF1 --

Column 28,
Line 47, change "[S(CH$_2$)" to -- [S(CH$_2$)$_{11}$ --

Column 34,
Line 14, change "comrises" to -- comprises --

Signed and Sealed this

Eighteenth Day of November, 2003

JAMES E. ROGAN
*Director of the United States Patent and Trademark Office*